United States Patent
Geary et al.

(10) Patent No.: US 9,347,061 B2
(45) Date of Patent: May 24, 2016

(54) ADMINISTERING ANTISENSE OLIGONUCLEOTIDES COMPLEMENTARY TO HUMAN APOLIPOPROTEIN B

(75) Inventors: Richard S. Geary, Carlsbad, CA (US); Zhengrong Yu, Carlsbad, CA (US); Mark K. Wedel, Temecula, CA (US); Diane Tribble, Carlsbad, CA (US)

(73) Assignee: Genzyme Corporation, Cambridge, MA (US)

( * ) Notice: Subject to any disclaimer, the term of this patent is extended or adjusted under 35 U.S.C. 154(b) by 542 days.

(21) Appl. No.: 12/532,602

(22) PCT Filed: Mar. 24, 2008

(86) PCT No.: PCT/US2008/058072
§ 371 (c)(1),
(2), (4) Date: Apr. 30, 2010

(87) PCT Pub. No.: WO2008/118883
PCT Pub. Date: Oct. 2, 2008

(65) Prior Publication Data
US 2010/0297105 A1    Nov. 25, 2010

Related U.S. Application Data

(60) Provisional application No. 60/896,914, filed on Mar. 24, 2007.

(51) Int. Cl.
*C12N 15/11* (2006.01)
*C12N 15/113* (2010.01)

(52) U.S. Cl.
CPC ........... *C12N 15/113* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 5,220,006 A | 6/1993 | Ross et al. | |
| 5,434,058 A | 7/1995 | Davidson | |
| 5,618,674 A | 4/1997 | Sanchez-Pescador et al. | |
| 5,656,612 A | 8/1997 | Monia | |
| 5,712,257 A | 1/1998 | Carter | |
| 5,786,206 A | 7/1998 | Smith et al. | |
| 5,801,154 A | 9/1998 | Baracchini et al. | |
| 5,877,009 A | 3/1999 | Zannis et al. | |
| 5,945,290 A | 8/1999 | Cowsert | |
| 5,998,148 A | 12/1999 | Bennett et al. | |
| 6,010,849 A | 1/2000 | Edwards et al. | |
| 6,033,910 A | 3/2000 | Monia et al. | |
| 6,096,516 A | 8/2000 | Kwak et al. | |
| 6,156,315 A | 12/2000 | Goldberg et al. | |
| 6,172,216 B1 | 1/2001 | Bennett et al. | |
| 6,184,212 B1 | 2/2001 | Miraglia et al. | |
| 6,235,470 B1 | 5/2001 | Sidransky | |
| 6,359,124 B1 | 3/2002 | Ecker et al. | |
| 6,448,079 B1 | 9/2002 | Monia et al. | |
| 6,500,672 B1 | 12/2002 | Sladek et al. | |
| 6,512,161 B1 | 1/2003 | Rouy et al. | |
| 6,534,277 B1 | 3/2003 | Hancock et al. | |
| 6,582,908 B2 | 6/2003 | Fodor et al. | |
| 6,660,737 B2 | 12/2003 | Almstead et al. | |
| 6,670,461 B1 | 12/2003 | Wengel et al. | |
| 6,852,536 B2 | 2/2005 | Dobie et al. | |
| 6,878,729 B2 | 4/2005 | Almstead et al. | |
| 6,949,367 B1 | 9/2005 | Dempcy et al. | |
| 7,407,943 B2 | 8/2008 | Crooke et al. | |
| 7,511,131 B2 | 3/2009 | Crooke et al. | |
| 7,598,227 B2 | 10/2009 | Crooke et al. | |
| 7,750,141 B2 | 7/2010 | Crooke et al. | |
| 7,803,930 B2 | 9/2010 | Crooke et al. | |
| 7,888,324 B2 | 2/2011 | Crooke et al. | |
| RE44,760 E | 2/2014 | Crooke et al. | |
| 8,673,871 B2 | 3/2014 | Bhanot et al. | |
| 8,735,364 B2 | 5/2014 | Crooke et al. | |
| 8,916,694 B2 | 12/2014 | Crooke et al. | |
| 2001/0053519 A1 | 12/2001 | Fodor et al. | |
| 2002/0068708 A1 | 6/2002 | Wengel et al. | |
| 2002/0123617 A1 | 9/2002 | Starling et al. | |
| 2003/0008373 A1 | 1/2003 | Bartel et al. | |
| 2003/0064950 A1 | 4/2003 | Ntambi et al. | |
| 2003/0083280 A1 | 5/2003 | Crooke et al. | |
| 2003/0087853 A1 | 5/2003 | Crooke et al. | |
| 2003/0096787 A1 | 5/2003 | Perricaudet et al. | |
| 2003/0215943 A1 | 11/2003 | Crooke et al. | |
| 2003/0228597 A1 | 12/2003 | Cowsert et al. | |
| 2003/0228613 A1 | 12/2003 | Bornarth et al. | |

(Continued)

FOREIGN PATENT DOCUMENTS

| EP | 0 332 435 | 9/1989 |
|---|---|---|
| EP | 0 530 794 | 3/1993 |

(Continued)

OTHER PUBLICATIONS

U.S. Appl. No. 60/159,462, Eggerman et al.
Agrawal et al., "Antisense therapeutics: is it as simple as complementary base recognition?" Molecular Medicine Today (2000) 6: 72-81.
Bennett et al., "Antisense Oligonucleotides as a Tool for Gene Functionalization and Target Validation," Biochimica et Biophysica Acta (1999) 1489:18-30.
Boren et al., "A simple and efficient method for making site-directed mutants, deletions, and fusions of large DNA such as P1 and BAC clones" Genome Research (1996) 11:1123-1130.
Branch et al., "A good antisense molecule is hard to find," TIBS (1998) 23:45-50.
Burnett, "Drug evaluation: ISIS-301012, an antisense oligonucleotide for the treatment of hypercholesterolemia" Current Opinion in Molecular Therapeutics (2006) 8(5):461-467.

(Continued)

*Primary Examiner* — J. E. Angell
(74) *Attorney, Agent, or Firm* — Jones Day

(57) ABSTRACT

Methods for long-term lowering of lipid levels in human subjects and for the treatment of conditions associated with elevated LDL-cholesterol and elevated ApoB are provided.

31 Claims, 3 Drawing Sheets

(56) References Cited

U.S. PATENT DOCUMENTS

Figure 1:
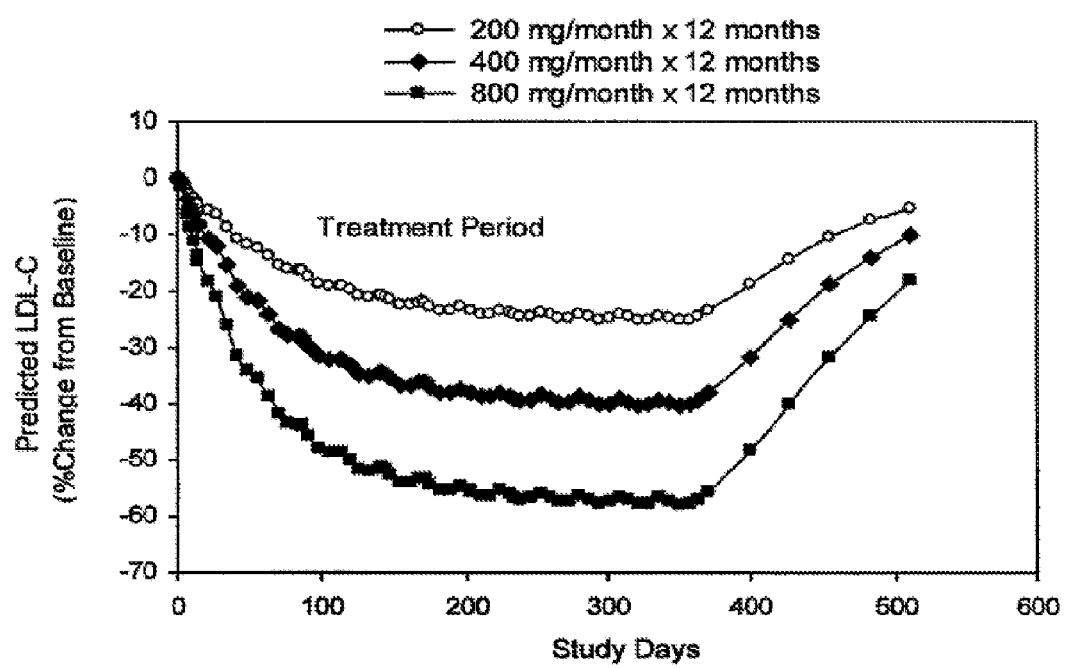

| | | |
|---|---|---|
| 2004/0171566 A1 | 9/2004 | Monia et al. |
| 2004/0208856 A1 | 10/2004 | Crooke et al. |
| 2004/0209838 A1 | 10/2004 | Monia et al. |
| 2004/0214325 A1 | 10/2004 | Crooke et al. |
| 2004/0241651 A1 | 12/2004 | Olek et al. |
| 2004/0266714 A1 | 12/2004 | Freier et al. |
| 2005/0009088 A1 | 1/2005 | Crooke et al. |
| 2005/0014713 A1 | 1/2005 | Freier |
| 2005/0043524 A1 | 2/2005 | Bhanot et al. |
| 2005/0130923 A1 | 6/2005 | Bhat et al. |
| 2005/0164271 A1 | 7/2005 | Bhanot et al. |
| 2005/0272680 A1 | 12/2005 | Bhanot et al. |
| 2005/0287558 A1 | 12/2005 | Crooke et al. |
| 2006/0009410 A1 | 1/2006 | Crooke et al. |
| 2006/0025373 A1 | 2/2006 | Bhanot et al. |
| 2006/0035858 A1 | 2/2006 | Geary |
| 2007/0031844 A1 | 2/2007 | Khvorova et al. |
| 2007/0087987 A1 | 4/2007 | Monia et al. |
| 2007/0238688 A1 | 10/2007 | Bhanot et al. |
| 2007/0238689 A1 | 10/2007 | Bhanot et al. |
| 2008/0146788 A1 | 6/2008 | Bhat et al. |
| 2008/0242629 A1 | 10/2008 | Crooke et al. |
| 2009/0306180 A1 | 12/2009 | Bhanot et al. |
| 2009/0326040 A1 | 12/2009 | Geary et al. |
| 2010/0297105 A1 | 11/2010 | Geary et al. |
| 2010/0331390 A1 | 12/2010 | Crooke et al. |
| 2011/0319469 A1 | 12/2011 | Crooke et al. |
| 2012/0115926 A1 | 5/2012 | Geary et al. |
| 2012/0129911 A1 | 5/2012 | Sacks et al. |
| 2015/0057329 A1 | 2/2015 | Bhanot et al. |
| 2015/0105440 A1 | 4/2015 | Crooke et al. |

FOREIGN PATENT DOCUMENTS

| | | |
|---|---|---|
| EP | 0 911 344 | 4/1999 |
| EP | 1 239 051 | 9/2002 |
| JP | 2002355074 | 12/2002 |
| WO | WO 92/10590 | 6/1992 |
| WO | WO 94/13794 A1 | 6/1994 |
| WO | WO 97/20924 | 6/1997 |
| WO | WO 97/35538 A2 | 10/1997 |
| WO | WO 98/20166 A2 | 5/1998 |
| WO | WO 98/32846 A2 | 7/1998 |
| WO | WO 98/36641 A1 | 8/1998 |
| WO | WO 99/14226 | 3/1999 |
| WO | WO 99/18237 A1 | 4/1999 |
| WO | WO 99/18986 A1 | 4/1999 |
| WO | WO 99/35241 A1 | 7/1999 |
| WO | WO 00/00504 A1 | 1/2000 |
| WO | WO 00/56916 A2 | 9/2000 |
| WO | WO 00/56920 A1 | 9/2000 |
| WO | WO 01/12789 A2 | 2/2001 |
| WO | WO 01/30354 A1 | 5/2001 |
| WO | WO 01/30395 A1 | 5/2001 |
| WO | WO 01/52902 A1 | 7/2001 |
| WO | WO 01/72765 A1 | 10/2001 |
| WO | WO 01/77384 A2 | 10/2001 |
| WO | WO 01/96586 | 12/2001 |
| WO | WO 02/22635 | 3/2002 |
| WO | WO 02/24717 | 3/2002 |
| WO | WO 02/26768 A2 | 4/2002 |
| WO | WO 03/011887 A2 | 2/2003 |
| WO | WO 03/074723 A2 | 9/2003 |
| WO | WO 03/097097 A1 | 11/2003 |
| WO | WO 03/097662 A1 | 11/2003 |
| WO | WO 2004/044181 A2 | 5/2004 |
| WO | WO 2004/046160 | 6/2004 |
| WO | WO 2004/077384 A1 | 9/2004 |
| WO | WO 2004/093783 | 11/2004 |
| WO | WO 2005/049621 A1 | 6/2005 |
| WO | WO 2006/020676 A2 | 2/2006 |
| WO | WO 2006/020676 A3 | 2/2006 |
| WO | WO 2007/031081 A2 | 3/2007 |
| WO | WO 2007/090071 A2 | 8/2007 |
| WO | WO 2007/131238 A2 | 11/2007 |
| WO | WO 2007/134181 | 11/2007 |
| WO | WO 2007/146511 | 12/2007 |
| WO | WO 2008/118883 A1 | 10/2008 |

OTHER PUBLICATIONS

Chin, A., "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Chapter 1: Basic Principles of Antisense Therapeutics" Antisense Research and Applications (1998) 131:1-50.

Crooke, "Antisense oligonucleotides as therapeutics for hyperlipidaemias" Expert Opinion on Biological Therapy (2005) 5(7):907-917.

Davidson et al., "Apolipoprotein B: mRNA editing, lipoprotein assembly, and presecretory degradation" Annu. Rev. Nutr. (2000) 20:169-193.

DeCatarina et al., "Fatty Acid Modulation of Endothelial Activation" American Journal of Clinical Nutrition (2000) 71(suppl.):213S-223S.

Deeb et al., "Chromosomal localization of the human apolipoprotein B gene and detection of homologous RNA in monkey intestine" Proc. Natl. Acad. Sci. USA (1986) 83:419-422.

De Mesmaeker et al., "Backbone modifications in oligonucleotides and peptide nucleic acid systems" Curr Opin Struct Biol (1995) 5:343-355.

Eggerman et al., "Use of Oligonucleotides to Target Nucleic Acid Sequences Encoding Apolipoprotein B to Decrease Serum Apolipoprotein B and Cholesterol Levels," Federal Register (2000) 65:110.

EMBL Accession No. A23827, Apr. 2, 1995.
EMBL Accession No. A13426, Oct. 5, 1994.
EMBL Accession No. A97152, Jan. 26, 2000.
EMBL Accession No. AR 152836, Aug. 9, 2001.
EMBL Accession No. I13154, Aug. 2, 1995.
EMBL Accession No. L27195, Jan. 6, 1994.
EMBL Accession No. L24258, Sep. 18, 1993.

Farese et al., "Knockout of the mouse apolipoprotein B gene results in embryonic lethality in homozygotes and protection against diet-induced hypercholesterolemia in heterozygotes" Proc. Natl. Acad. Sci. USA (1995) 92:1774-1778.

Fluiter K., et al., "On the in vitro and in vivo properties of four locked nucleic acid nucleotides incorporated into an anti-h-ras antisense oligonucleotide," Chembiochem—A European Journal of Chemical Biology, (2005) 6(6): 1104-1109.

Frieden M., et al, "Expanding the design horizon of antisense oligonucleotides with alpha-L-LNA," Nucleic Acids Research, Oxford University Press, Surrey, GB, (2003) 31(21): 6365-6372.

Ganji et al., "Niacin and cholesterol: role in cardiovascular disease (Review)" The Journal of Nutritional Biochemistry (2003) 14:293-305.

Geary et al., "Pharmacokinetics of a Tumor Necrosis Factor-α Phosphorothioate 2'-O(2-Methoxyethyl) Modified Antisense Oligonucleotide: Comparison Across Species," Drug Metab Dispos (2003):31:1419-1428.

Genbank Accession No. NM_000384, Oct. 31, 2000, Huang et al.
Geneseq Accession No. AAA07969, Jan. 29, 2001.
Geneseq Accession No. AAA28208, Jan. 29, 2001.
Geneseq Accession No. AAV39607, Sep. 28, 1998.
Geneseq Accession No. AAX89306, Sep. 21, 1999. (from WO 99/35241).

Graham et al., "Inhibition of ApoB-100 as a Therapeutic Strategy for the Treatment of Hyperlipidemias" AHA Abstracts (2002) Abstract ID:20009.

Graham et al., "Pharmacological Inhibition of PCSK9 in Hyperlipiemic Mice Significantly Reduces Serum LDL-C While Increasing Hepatic Low-Density Lipoprotein Receptor Protein Abundance," Jun. 2007, 27(6), p. E36.

Hajjar et al., "The role of lipoprotein(a) in atherogenesis and thrombosis" Annu. Rev. Med. (1996) 47:423-442.

(56) References Cited

OTHER PUBLICATIONS

Hammond et al., "Post-transcriptional gene silencing by double-stranded RNA" Nature Reviews Genetics (2001) 2:110-119.
Huang et al., "Hypobetalipoproteinemia due to an apolipoprotein B gene exon 21 deletion derived by Alu-Alu recombination" Journal of Biological Chemistry (1989) 264:11394-11400. (Genbank NM_000384).
Iijima et al., "Red Wine Polyphenols Inhibit Vascular Smooth Muscle Cell Migration Through Two Distinct Signaling Pathways" Circulation (2002) 105(20):2404-2410.
Innerarity et al., "Familial defective apolipoprotein B-100: low density lipoproteins with abnormal receptor binding" Proc. Natl. Acad. Sci. USA (1987) 84:6919-6923.
James, W., "Towards gene-inhibition therapy; a review of progress and prospects in the field of antiviral antisense nucleic acids and ribozymes," Antiviral Chemistry and Chemotherapy, (1991) 2(4):191-214.
Jen et al., "Suppression of Gene Expression by Targeted Disruption of Messenger RNA: Available Options and Current Strategies" Stem Cells (2000) 18:307-319.
Kastelein et al., "Potent reduction of apolipoprotein B and low-density lipoprotein cholesterol by short-term administration of an antisense inhibitor of apolipoprotein B" Circulation (2006) 114(16):1729-1735.
Katan et al., "Characteristics of human hypo- and hyperresponders to dietary cholesterol" Am. J. Epidemiol. (1987) 125:387-399.
Kim et al., "Genetically modified mice for the study of apolipoprotein B," J. Lipid Res. (1998) 39:703-723.
Koba et al., "Small dense LDL phenotype is associated with postprandial increases of large VLDL and remnant-like particles in patients with acute myocardial infarction" Atherosclerosis (2003) 170:131-140.
Latorra et al., "Enhanced allele-specific PCR discrimination in SNP genotyping using 3' locked nucleic acid (LNA) primers," Human Mutation (2003) 22:79-85.
Law et al., "Human apolipoprotein B-100: cloning, analysis of liver mRNA, and assignment of the gene to chromosome 2," Proc. Natl. Acad. Sci. USA (1985) 82:8340-8344.
Lemonidis, et al., "Abstracts of the 11$^{th}$ International Congress on Cardiovascular Pharmacotherapy. Montreal, Canada, May 18-21, 2002," Cardiovascular Drugs and Therapy/Sponsored by the International Society of Cardiovascular Pharmacotherapy (2002) vol. 16, Suppl. 1, P471, SP002565482.
Ma et al., "Synthetic oligonucleotides as therapeutics: the coming age," Biotechnology Annual Review (2000) 5:155-196.
Maxwell et al., "Proprotein Convertase Subtilisin Kexin 9: The Third Locus Implicated in Autosomal Dominant Hypercholesterolemia," Current Opinion in Lipidology (2005) vol. 16, pp. 167-172.
McCormick et al., "Transgenic mice expressing human ApoB95 and ApoB97. Evidence that sequences within the carboxyl-terminal portion of human apoB100 are important for the assembly of lipoprotein," J. Biol. Chem. (1997) 272:23616-23622.
Milner et al., "Selecting effective antisense reagents on combinatorial oligonucleotide arrays," Nature Biotechnology, Jun. 1997, vol. 15:537-541.
NCBI Search Results, (ISPH-0592) dated Oct. 30, 2007, Mamm. Genom (1995) vol. 6 (3):192-195.
New England Biolabs, 1998/1999 Catalog, pp. 121 and 284.
Nishina et al., "Synthetic low and high fat diets for the study of atherosclerosis in the mouse," J. Lipid Res. (1990) 31:859-869.
Nowak-Gottl et al., "Lipoprotein (a): its role in childhood thromboembolism," Pediatrics (1997) 99:1-3.
Parrish et al., "Functional anatomy of a dsRNA trigger: differential requirement for the two trigger strands in RNA interference," Molecular Cell (2000) 6:1077-1087.
Patil et al., "DNA-based therapeutics and DNA delivery systems: a comprehensive review," AAPS Journal (2005) 7:E61-E77.
Petersen et al., "Locked nucleic acid (LNA) recognition of RNA: NMR solution structures of LNA:RNA hybrids," Journal of the American Chemical Society (2002) 124:5974-5982.
PR Newswire, "Isis Pharmaceuticals initiates phase I study of second-generation antisense drug for cardiovascular disease" New York, Dec. 29, 2003.
Rojanasakul, Y, "Antisense Oligonucleotide Therapeutics: Drug Delivery and Targeting," Advanced Drug Delivery Reviews (1996) vol. 18, pp. 115-131, XP002913878.
Rosenson, "Clinical Role of LDL and HDL Subclasses and Apoliprotein Measurements," ACC Current Journal Review (2004): 33-37.
Rossi et al., "Introductory Remarks on the General Application of Antisense RNAs and Ribozymes," Methods: A Companion to Methods in Enzymology (1993) 5:1-5.
Rubies-Prat et al., "Low-density lipoprotein particle size, triglyceride-rich lipoproteins, and glucose tolerance in non-diabetic men with essential hypertension" Clinical and Experimental Hypertension (2001) vol. 23:489-500.
Sandkamp et al., "Lipoprotein(a) is an independent risk factor for myocardial infarction at a young age," Clin. Chem. (1990) 36:20-23.
Seed et al., "Relation of serum lipoprotein(a) concentration and apolipoprotein(a) phenotype to coronary heart disease in patients with familial hypercholesterolemia," N Engl J Med (1990) 322:1494-1498.
Senior, "Antisense inhibitor provides new treatment approach for hypercholesterolaemia" Drug Discovery Today (2002) 7:840-841.
Sewell et al.., "Phase I Trial of ISIS 104838, a 2'-Methoxyethyl Modified Antisense Oligonucleotide Targeting Tumor Necrosis Factor-α," The Journal of Pharmacology and Experimental Therapeutics (2002) 303:1334-1343.
Simeonov et al., "Single nucleotide polymorphism genotyping using short, fluorescently labeled locked nucleic acid (LNA) probes and fluorescence polarization detection," Nucleic Acids Research (2002) 30:E91.
Skrapari et al., "Glibenclamide improves postprandial hypertriglyceridaemia in type 2 diabetic patients by reducing chylomicrons but not the very low-density lipoprotein subfraction levels," Diabet Med (2001) 18:781-785.
Smith et al., "Rational selection fo antisense oligonucleotide sequences," European Journal of Pharmaceutical Sciences (2000) vol. 11, No. 3, 191-198, XP002372482.
Tanaka et al., "Regulation of apolipoprotein B production and secretion in response to the change of intracellular cholesteryl ester contents in rabbit hepatocytes," Journal of Biological Chemistry (1993) 268:12713-12718.
Tang et al., "The Inhibition of Antisense Oligodeoxynucleotides on the Expression of Apolipoprotein B in Rat Liver Cells," Zhongguo Dongmai Yinghua ZaZhi Bianjibu (Chinese Journal) (1999) 7:315-318.
Veniant et al., "Susceptibility to atherosclerosis in mice expressing exclusively apolipoprotein B48 or apolipoprotein B100," J. Clin. Invest. (1997) 100:180-188.
Vessby et al., "Diverging effects of cholestyramine on apolipoprotein B and lipoprotein Lp(a). A dose-response study of the effects of cholestyramine in hypercholesterolaemia," Atherosclerosis (1982) 44:61-71.
Wimberly, "Rosuvastatin (Crestor) A new statin for the treatment of dyslipidemia" PharmaNote (2003) 19:1-6.
Yu et al., "Pharmacokinetics and Pharmacodynamics of an Antisense Phosphorothioate Oligonucleotide Targeting Fas mRNA in Mice," J. Pharmacol. Exp. Ther. (2001) vol. 296-388-395.
Yu et al., "Antisense oligonucleotide inhibition of DGAT2 expression reduced hepatic steatosis diet-induded obese mice," Obesity Research (2003) vol. 11(Suppl), p. A48.
Yu et al., "Antisense oligonucleotide reduction of DGAT2 expression improves hepatic steatosis and hyperlipidemia in obese mice," Hepatology (2005) vol. 42, No. 2, pp. 362-371.
Advisory Action for U.S. Appl. No. 10/712,795 dated Apr. 28, 2008.
Final Rejection Office Action for U.S. Appl. No. 10/712,795 dated Apr. 9, 2007.
Final Rejection Office Action for U.S. Appl. No. 10/712,795 dated Jan. 8, 2008.
Office Action for U.S. Appl. No. 10/712,795 dated Apr. 14, 2006.
Office Action for U.S. Appl. No. 10/712,795 dated Oct. 10, 2006.
Office Action for U.S. Appl. No. 10/712,795 dated Jul. 26, 2007.

(56) References Cited

OTHER PUBLICATIONS

Advisory Action for U.S. Appl. No. 10/920,612 dated Oct. 16, 2007.
Advisory Action for U.S. Appl. No. 10/920,612 dated Feb. 26, 2009.
Final Rejection Office Action for U.S. Appl. No. 10/920,612 dated Mar. 28, 2007.
Final Rejection Office Action for U.S. Appl. No. 10/920,612 dated Aug. 7, 2008.
Office Action for U.S. Appl. No. 10/920,612 dated Aug. 8, 2006.
Office Action for U.S. Appl. No. 10/920,612 dated Dec. 12, 2007.
Office Action for U.S. Appl. No. 11/123,656 dated Jun. 13, 2007.
Office Action for U.S. Appl. No. 11/123,656 dated Dec. 13, 2007.
Office Action for U.S. Appl. No. 11/123,656 dated Dec. 3, 2008.
Office Action dated Sep. 9, 2009 for U.S. Appl. No. 11/123,6556.
Advisory Action for U.S. Appl. No. 11/200,710 dated Sep. 13, 2007.
Final Rejection Office Action for U.S. Appl. No. 11/200,710 dated May 15, 2007.
Final Rejection Office Action for U.S. Appl. No. 11/200,710 dated Jan. 13, 2009.
Office Action for U.S. Appl. No. 11/200,710 dated Sep. 28, 2006.
Office Action for U.S. Appl. No. 11/200,710 dated May 21, 2008.
Non-final Office Action dated Apr. 15, 2010 for U.S. Appl. No. 11/200,710.
Non-final Office Action dated Jun. 18, 2010 for U.S. Appl. No. 11/573,537.
Advisory Action for U.S. Appl. No. 09/920,033 dated Feb. 28, 2006.
Advisory Action for U.S. Appl. No. 09/920,033 dated Jun. 1, 2007.
Final Rejection Office Action for U.S. Appl. No. 09/920,033 dated Jul. 22, 2003.
Final Rejection Office Action for U.S. Appl. No. 09/920,033 dated Oct. 4, 2005.
Final Rejection Office Action for U.S. Appl. No. 09/920,033 dated Jan. 12, 2007.
Final Rejection Office Action for U.S. Appl. No. 09/920,033 dated Jan. 7, 2009.
Office Action for U.S. Appl. No. 09/920,033 dated Jan. 14, 2003.
Office Action for U.S. Appl. No. 09/920,033 dated Jan. 13, 2004.
Office Action for U.S. Appl. No. 09/920,033 dated Aug. 5, 2004.
Office Action for U.S. Appl. No. 09/920,033 dated Jan. 19, 2005.
Office Action for U.S. Appl. No. 09/920,033 dated Jun. 26, 2006.
Office Action for U.S. Appl. No. 09/920,033 dated Feb. 7, 2008.
Office Action for U.S. Appl. No. 09/920,033 dated Sep. 8, 2009.
Final Rejection Office Action for U.S. Appl. No. 10/147,196 dated Mar. 24, 2004.
Final Rejection Office Action for U.S. Appl. No. 10/147,196 dated Feb. 1, 2005.
Final Rejection Office Action for U.S. Appl. No. 10/147,196 dated May 17, 2006.
Office Action for U.S. Appl. No. 10/147,196 dated Jul. 11, 2003.
Office Action for U.S. Appl. No. 10/147,196 dated Aug. 12, 2004.
Office Action for U.S. Appl. No. 10/147,196 dated Aug. 17, 2005.
Office Action for U.S. Appl. No. 10/147,196 dated Jan. 25, 2007.
Final Rejection Office Action for U.S. Appl. No. 11/124,020 dated Jul. 30, 2010.
Advisory Action for U.S. Appl. No. 11/124,020 dated Aug. 11, 2009.
Final Rejection Office Action for U.S. Appl. No. 11/124,020 dated Jan. 26, 2009.
Office Action for U.S. Appl. No. 11/124,020 dated Jan. 14, 2008.
Non-final Office Action dated Dec. 2, 2009 for U.S. Appl. No. 11/124,020.
Non-final Office Action dated Oct. 28, 2009 for U.S. Appl. No. 11/969,096.
Final Office Action dated Jul. 15, 2010 for U.S. Appl. No. 11/969,096.
ISA, International Search Report dated Aug. 31, 2004 for application No. PCT/US03/36411.
EPO, Supplementary Partial European Search Report for Application No. 03789763.4 dated Jul. 26, 2006.
EPO, Supplementary European Search Report for Application No. 03789763.4 dated Jul. 26, 2006.
ISA, International Search Report dated Apr. 10, 2006 for Application No. PCT/US05/028342.
ISA, International Search Report for Application PCT /US00/29223 dated Dec. 26, 2000.
EPO, Supplementary Partial European Search Report for application No. 027761201.9 dated Jul. 3, 2006.
EPO, Supplementary European Search Report for PCT/US02/24247 dated Oct. 13, 2006.
EPO, European Search Report dated Feb. 8, 2010 for application No. 09015376.8.
ISA, International Search Report dated Oct. 22, 2003 for Application No. PCT/US03/15493.
ISA, International Search Report for dated Jul. 28, 2008 Application PCT/US08/058072.
ISA, International Search Report dated Apr. 21, 2008 for Application No. PCT/US07/68401.
ISA,Communication Relating to the Results of the Partial International Search PCT/US07/68401 dated Jan. 30, 2008.
ISA, International Search Report dated Mar. 13, 2008 for Application PCT/US07/68403.
ISA, International Search Report dated Mar. 13, 2008 for Application PCT/US07/68404.
ISA, International Search Report dated Apr. 24, 2008 for Application PCT/US07/68410.
ISA, International Search Report dated Apr. 24, 2008 for Application PCT/US07/68412.
ISA, International Search Report dated Apr. 25, 2008 for Application PCT/US07/68415.
Elias et al., "Decreased Production Rates of VLDL Triglycerides and ApoB-100 in Subjects Heterozygous for Familial Hypobetalipoproteinemia," Metabolism of Triglycerides and ApoB-100 n FHBL, *Arterioscler Therob Vasc Biol.*, (1999)9:2714-2721.
Sniderman et al., "Substrate Delivery as a Determinant of Hepatic ApoB Secretion," *Arterioscler Thromb Vasc Biol.*, (1993)13:629-636.
Yu et al., "Pharmacokinetics and Pharmacodynamics of an Antisense Phosphorothioate Oligonucleotide Targeting Fas mRNA in Mice," *J. Pharmacol. Exp. Ther.* (2001)296(2):388-395.
Hungarian Patent Office, Written Opinion to International Property Office of Singapore dated Oct. 22, 2010.
EPO, European Search Report dated May 3, 2011 for application No. 10180483.9.
Ostrander et al., "Dog (Clone: CXX.371) Primer for STS 371, 5' End, Sequence Tagged Site," EMBL XP002392182, Sep. 18, 1993.
Ostrander et al., "Dog Primer for STS 610, 3' End, Sequence Tagged Site," EMBL XP002392183, Jan. 6, 1994.
Bayarsaihan et al., "Single-strand-DNA-binding factors specifically recognize the pyrimidine element in the chick a2(I) collagen gene promoter" Biochem J. (1996) 314:293-296.
Bennett et al., "Inhibition of endothelial cell adhesion molecule expression with antisense oligonucleotides." Journal of Immunology (1994) 152(7):3530-3540.
Bonow, "Primary Prevention of Cardiovascular Disease: A Call to Action" Circulation (2002) 106:3140-3141.
Braasch et al., "Novel Antisense and Peptide Nucleic Acid Strategies for Controlling Gene Expression," Biochemistry 41:4503-4510 (2002).
Bradley et al., "Small, dense, LDL particle concentration is significantly reduced after treatment with an antisense inhibitor of ApoB in health volunteers" Circulation (2005) 112(17) Suppl. pp. I1-133/II.
Campos et al., "Distinct patterns of lipoproteins with apoB defines by presence of apoE or apoC-III in hypercholesterolemia and hypertriglyceridemia" J. Lipid Res. (2001) 42:1239-13491.
Chan et al., "Apolipoprotein B-100 kinetics in visceral obesity: Associations with plasma apolipoprotein C-III concentration," Metabolism Clin. and Experimental (2002) 51(8):1041-1046.
Crooke, "Progress in Antisense Technology" Ann. Rev. Med. (2004) 55:61-95.
Cuchel et al., "Inhibition of Microsomal Triglyceride Transfer Protein in Familial Hypercholesterolemia" New England Journal of Medicine (2007) 356:148-156.

(56) References Cited

OTHER PUBLICATIONS

Dammerman et al., "An apolipoprotein CIII haplotype protective against hypertriglyceridemia is specified by promoter and 3' untranslated region polymorphisms" Proc. Natl. Acad. Sci. U. S. A., (1993) 90:4562-4566.
Davis et al., "Atherosclerosis is a Liver Disease of the Heart" Arterioscler. Thromb. Vasc. Biol. (2001) 21:887-898.
De Silva et al., "Overexpression of human apolipoprotein C-III in transgenic mice results in an accumulation of apolipoprotein B48 remnants that is corrected by excess apolipoprotein E" J. Biol. Chem. (1994) 269:2324-2335.
Deere et al., "Antisense Phosphorodiamidate Morpholino Oligomer Length and Target Position Effects on Gene-Specific Inhibition in *Escherichia coli*" Antimicrobial Agents and Chemotherapy (2005) 49:249-255.
Dixon et al., "Regulation of hepatic secretion of apolipoprotein B-containing lipoproteins: Information obtained from cultured liver cells" J. Lipid Res. 34:167-179 (1993).
Duivenvoorden et al., "Apolipoprotein C3 Deficiency Results in Diet-Inudced Obesity and Aggravated Insulin Resistance in Mice" Diabetes (2005) 54:664-671.
Flaim et al., "A Phase 1 Study in Healthy Volunteers to Evaluate the Pharmokinetics, Safety, and Tolerability of Mipomersen in Three Dosing Regimens" Poster Presentation (2011).
Funatsu et al., "Reduction in hepatic non-esterified fatty acid concentration after long-term treatment with atorvastatin lowers hepatic triglyceride synthesis and its secretion in sucrose-fed rats" Biochimica et Biophysica Acta (2002) 1580:161-170.
Gautschi et al., "Activity of a Novel bcl-2/bcl-xL-Bispecifc Antisense Oligonucleotide Against Tumors of Diverse Histologic Origins" J. Natl Cancer Inst (2001) 93:463-471.
Gewirtz et al., "Facilitating oligonucleotide delivery: Helping antisense deliver on its promise" PNAS USA (1996) 93:3161-3163.
Hertz et al., "Mode of action of peroxisome proliferators as hypolipidemic drugs. Suppression of apolipoprotein C-III" J. Biol. Chem. (1995) 270:13470-13475.
Heymsfield, "Effects of Weight Loss With Orlistat on Glucose Tolerance and Progression to Type 2 Diabetes in Obese Adults" Archives of Internal Medicine 160:1321-1326 (2000).
ISA, International Search Report dated May 25, 2010 for Application PCT/US10/27541.
"Isis 301012" retrieved from the intenet: URL: http://integrity.thomson-pharma.com/integrity/xmlxsl/pk_ref_list.xml_show_ficha_ref?p_refid=1132978 [retrieved Nov. 29, 2012].
Ito et al., "Hypertriglyceridemia as a result of human apo CIII gene expression in transgenic mice" Science (1990) 249:790-793.
Jong et al., "Role of ApoCs in Lipoprotein Metabolism—Functional Differences Between ApoC1, ApoC2, and ApoC3" Arterioscler. Thromb. Vasc. Biol. (1999) 19:472-484.
Jover et al., "Cytochrome P450 regulation by hepatocyte nuclear factor 4 in human hepatocytes: a study using adenovirus-mediated antisense targeting" Hepatology (2001) 33(3):668-675.
Karathanasis, "Apolipoprotein multigene family: tandem organization of human apolipoprotein AI, CIII, and AIV genes" Proc. Natl. Acad. Sci. U. S. A. (1985) 82:6374-6378.
Kardassis et al., "Direct physical interactions between HNF-4 and Sp1 mediate synergistic transactivation of the apolipoprotein CIII promoter" Biochemistry (2002) 41:1217-1228.
Kardassis et al., "SMAD proteins transactivate the human ApoCIII promoter by interacting physically and functionally with hepatocyte nuclear factor 4" J. Biol. Chem. (2000) 275:41405-41414.
Kawakami et al., Apolipoprotein CIII in Apolipoprotein B Lipoproteins Enhances the Adhesion of Human Monocytic Cells to Endothelial Cells, Circulation (2006) 113:691-700.
Klein et al., "P284: Apoprotein C-III (ApoCIII) Protein Concentrations and Gene Polymorphisms in Type 1 Diabetes" Aretioscler. Thromb. Vasc. Biol. (2002) 22(5):A-50.
Knopp, "Drug Treatment of Lipid Disorders" New Engl J. Med (1999) 341:498-511.
Lai et al., "Association between obesity and hyperlipidemia among children." Yale Journal of Biology and Medicine (2001) 74:205-210.
Lee et al., "LDL Containing Apolipoprotein CIII Is an Independent Risk Factor for Coronary Events in Diabetic patients" Arteriosclerosis, Thrombosis, and Vascular Biology (2003) 23:853-858.
Levy-Wilson et al., "Isolation and DNA sequence of full-length cDNA for human preapolipoprotein CIII" DNA (1984) 3:359-364.
Li et al., "Common genetic variation in the promoter of the human apo CIII gene abolishes regulation by insulin and may contribute to hypertriglyceridemia" J. Clin. Invest. (1995) 96:2601-2605.
Maeda et al., "Molecular cloning of a human apo-C-III variant: Thr 74—Ala74 mutation prevents O-glycosylation" J. Lipid Res. (1987) 28:1405-1409.
Maeda et al., "Targeted disruption of the apolipoprotein C-III gene in mice results in hypotriglyceridemia and protection from postprandial hypertriglyceridemia" J. Biol. Chem. (1994) 269:23610-23616.
Merki et al., "A second generation antisense oligonucleotide directed to human apolipoprotein B-100 reduces lipoprotein(a) levels and oxidized phospholipids on apolipoprotein B-100 particles in lipoprotein(a)-transgenic mice," J. Amer. Coll. Cardiol. (2008) 51(1) Suppl. 1, A294.
Merki et al., "Antisense oligonucleotide directed to human apolipoprotein B-100 reduces lipoprotein(a) levels and oxidized phospholipids on apolipoprotein B-100 particles in lipoprotein(a)-transgenic mice, " Circulation (2008) 118:743-753.
Nielsen, "Systemic Delivery: The Last Hurdle?" Gene Therapy (2005) 12:956-957.
Ogami et al., "Purification and characterization of a heat stable nuclear factor (CIIIB1 involved in the regulation of the human ApoC-III gene" J. Biol. Chem. (1991) 266:9640-9646.
Olivieri et al., "ApoC-III polymorphisms and risk of coronary artery disease" J. Lipid Res. (2002) 43: 1450-1457.
Olivieri et al., "Apolipoprotein C-III, n-3 Polyunsaturated Fatty Acids, and "Insulin_Resistant" T-455C APOC3 Gene Polymorphisms in Heart Disease Patients: Exapmle of Gene-Diet Interaction" Clin. Chem. (2005) 51(2):360-367.
Opalinska et al., "Nucleic-Acid Therapeutics: Basic Principles and Recent Applications" Nature Rev. Drug Discov. (2002) 1:503-514.
Pittner et al., "Effects of PYY[3-36] in rodent models of diabetes and obesity" Int. J. Obes. Relat. Metab. Disord. (2004) 28:963-971.
PR Newswire, "Second generation antisense drug for cardiovascular disease demonstrates significant durable reductions in cholesterol" New York, Aug. 11, 2004; Source: Isis Pharmaceuticals.
Protter et al., "Isolation and sequence analysis of the human apolipoprotein CIII gene and the intergenic region between the apo AI and apo ACIII genes" DNA (1984) 3:449-456.
Raspe et al., "Identification of Rev-erbalpha as a physiological repressor of apoC-III gene transcription" J. Lipid Res. (2002) 43:2172-2179.
Reynolds et al., "Rational siRNA design for RNA interference" Nature Biotechnology (2004) 22(3):326-330.
Roglans et al., "Atorvastatin Treatment Induced Peroxisome Proliferator-Activated Receptor Alpha Expression and Decreased Plasma Nonesterified Fatty Acids and Liver Triglyceride in Fructose-Fed Rats" Journal of Pharmacology and Experimental Therapeutics (2002) 302:232-239.
Sanghvi et al., "Heterocyclic Base Modifications in Nucleic Acids and Their Applications in Antisense Oligonucleotides" Antisense Research and Applications (1993) pp. 273-288.
Schoonjans et al., "3-Hydroxy-3-methylglutaryl CoA reductase inhibitors reduce serum triglyceride levels through modulation of apolipoprotein C-III and lipoprotein lipase" FEBS Lett. (1999) 452:160-164.
Shachter, "Apolipoproteins C-I and C-III as important modulators of lipoprotein metabolism" Curr. Opin. Lipidol. (2001) 12:297-304.
Sharpe et al., "Human apolipoproteins AI, AII, CII and CIII cDNA sequences and mRNA abundance" Nucleic Acids Res. (1984) 12:3917-3932.
Tamm et al., "Antisense therapy in oncology: new hope for an old idea?" The Lancet (2001) 358:489-497.
Ugawa et al., "YM-53601, a novel squalene synthase inhibitor, suppresses lipgenic biosynthesis and lipid secretion in rodents" British Journal of Pharmacology (2003) 139:140-146.

(56) References Cited

OTHER PUBLICATIONS

Vu-Dac et al., "Retinoids increase human apo C-III expression at the transcriptional level via the retinoid X receptor. Contribution to the hypertriglyceridemic action of retinoids." J. Clin. Invest. (1998) 102:625-632.

Woolf et al., "Specificity of antisense oligonucleotides in vivo" PNAS (1992) 89:7305-7309.

Yamamoto et al., "Overexpression of PACAP in Transgenic Mouse Pancreatic B-Cells Enhances Insulin Secretion and Ameliorates Streptozotocin-induced Diabetes" Diabetes (2003) 52:1155-1162.

Zhengming et al., "Serum cholesterol concentration and coronary heart disease in population with low cholesterol concentrations" BMJ. (1991) 303:276-282.

ADMINISTERING ANTISENSE OLIGONUCLEOTIDES COMPLEMENTARY TO HUMAN APOLIPOPROTEIN B

CROSS REFERENCE TO RELATED APPLICATIONS

This application is a U.S. National Stage application of International Application No. PCT/US2008/058072, filed 24 Mar. 2008, which claims the priority benefit of U.S. Patent Application No. 60/896,914 filed 24 Mar. 2007, the contents of which are incorporated herein by reference in their entirety.

FIELD OF THE INVENTION

The present invention provides compositions and methods for lowering LDL-cholesterol and treatment of conditions associated with elevated cholesterol levels. More specifically, the invention relates to compositions and methods for inhibiting apolipoprotein B expression in the liver.

BACKGROUND OF THE INVENTION

Coronary heart disease (CHD) has been the leading cause of death in the United States for over a century, and complications from atherosclerosis are the most common causes of death in Western societies (Knopp, New Engl. J. Medicine, 1999, 341, 498-511; Davis and Hui, Arterioscler. Thromb. Vasc. Biol., 2001, 21, 887-898; Bonow, Circulation, 2002, 106, 3140-3141). Elevated low density lipoprotein-cholesterol (LDL-cholesterol) is widely recognized as a risk factor for CHD. However, despite pharmacologic intervention, many subjects are unable to lower LDL-cholesterol levels.

The guidelines for lipid lowering therapy were established by the Adult Treatment Panel III of the National Cholesterol Education Program (NCEP) in 2001. Modifications to these guidelines were recommended by the Coordinating Committee of the NCEP in 2004, and included more aggressive treatment goals (Grundy et al., Circulation, 2004, 110, 227-239). These guidelines define 3 categories of risk for major coronary events and provide desirable LDL-cholesterol target levels. Those at highest risk are subjects with CHD or CHD risk equivalent and should maintain LDL-cholesterol below 100 mg/dL. The most recent NCEP guidelines recommend that subjects at very high risk for CHD use drug therapy to achieve LDL-cholesterol levels of less than 70 mg/dL. CHD equivalent is defined as subjects with diabetes, peripheral vascular disease, abdominal aortic aneurysm, symptomatic carotid artery disease, and those with multiple risk factors that confer a 10 year risk for CHD greater than 20%. For the second category, those subjects at moderately high risk for CHD with multiple (2 or more) risk factors in whom the 10 year risk for CHD is 20%, the goal is LDL-cholesterol of less than 130 mg/dL. The most recent recommendations include a therapeutic option to lower LDL-cholesterol levels to less than 100 mg/dL in the moderately high-risk category. The third category includes subjects with 0-1 risk factors and the target LDL-cholesterol is less than 160 mg/dL. The risk factors include age, cigarette smoking, hypertension, low HDL-cholesterol, and family history of CHD. Drug therapy should be initiated when serum LDL-cholesterol remains above 130, 160 and 190 mg/dL in the 3 risk groups, respectively, despite therapeutic lifestyle changes (Grundy et al., Circulation, 2004, 110, 227-239).

Low density lipoproteins are one of five broad classes of lipoproteins, which include the following: chylomicrons, responsible for the transport dietary lipids from intestine to tissues; very low density lipoproteins (VLDL); intermediate density lipoproteins (IDL); low density lipoproteins (LDL); all of which transport triacylglycerols and cholesterol from the liver to tissues; and high density lipoproteins (HDL), which transport endogenous cholesterol from tissues to the liver. Lipoprotein particles undergo continuous metabolic processing and have variable properties and compositions. The protein components of lipoproteins are known as apolipoproteins. At least nine apolipoproteins, one of which is apolipoprotein B, are distributed in significant amounts among the various human lipoproteins.

Apolipoprotein B (also known as ApoB, apolipoprotein B-100; ApoB-100, apolipoprotein B-48; ApoB-48 and Ag(x) antigen), is a large glycoprotein involved in the assembly and secretion of lipids and in the transport and receptor-mediated uptake and delivery of distinct classes of lipoproteins. Apolipoprotein B performs a variety of functions, including the absorption and processing of dietary lipids, as well as the regulation of circulating lipoprotein levels (Davidson and Shelness, Annu. Rev. Nutr., 2000, 20, 169-193).

Two forms of apolipoprotein B exist in mammals. ApoB-100 represents the full-length protein containing 4536 amino acid residues, synthesized primarily in the human liver (Davidson and Shelness, Annu. Rev. Nutr., 2000, 20, 169-193). A truncated form known as apoB-48 is colinear with the amino terminal 2152 residues and is synthesized in the small intestine of all mammals (Davidson and Shelness, Annu. Rev. Nutr., 2000, 20, 169-193). In humans, apoB-48 circulates in association with chylomicrons and chylomicron remnants and these particles are cleared by a distinct receptor known as the LDL-receptor-related protein (Davidson and Shelness, Annu. Rev. Nutr., 2000, 20, 169-193). ApoB-48 can be viewed as an adaptation by which dietary lipid is delivered from the small intestine to the liver, while apoB-100 participates in the transport and delivery of cholesterol (Davidson and Shelness, Annu. Rev. Nutr., 2000, 20, 169-193). ApoB is the major protein component of LDL and contains the domain required for interaction of this lipoprotein species with the LDL receptor. In addition, ApoB contains an unpaired cysteine residue which mediates an interaction with apolipoprotein(a) and generates lipoprotein(a) or Lp(a), another distinct lipoprotein with atherogenic potential (Davidson and Shelness, Annu. Rev. Nutr., 2000, 20, 169-193). Elevated plasma levels of the ApoB-containing lipoprotein Lp(a) are associated with increased risk for atherosclerosis and its manifestations, which may include hypercholesterolemia (Seed et al., N. Engl. J. Med., 1990, 322, 1494-1499), myocardial infarction (Sandkamp et al., Clin. Chem., 1990, 36, 20-23), and thrombosis (Nowak-Gottl et al., Pediatrics, 1997, 99, E11).

Apolipoprotein B is involved cholesterol homeostasis and its overproduction has been associated with various diseases, including familial hypercholesterolemia, familial defective ApoB and familial combined hypercholesterolemia (Kane and Havel, The Metabolic and Molecular Bases of Inherited Diseases, 2001, 8$^{th}$ edition, 2717-2751). Perturbations in the metabolism of ApoB that correspond with an increased risk of CHD are also observed in diabetes and obesity (Grundy, Am. J. Cardiol., 1998, 81, 18B-25B; Chan et al., Diabetes, 2002, 51, 2377-2386; Chan et al., Metabolism, 2002, 51, 1041-1046). Furthermore, genetic studies in mouse models have demonstrated a correlation between elevated apolipoprotein B, elevated cholesterol levels and atherosclerosis (Kim and Young, J. Lipid Res., 1998, 39, 703-723; Nishina et al., J. Lipid Res., 1990, 31, 859-869).

In studies of subjects with familial hypobetalipoproteinemia (FHBL), these subjects exhibit lowered serum apolipoprotein B levels, lowered serum LDL-cholesterol levels and a reduced incidence of coronary artery disease (Schonfeld et al., *J. Lipid Res.*, 2003, 44, 878-883). Murine studies have demonstrated that mice having heterozygous deficiencies in apolipoprotein B exhibit reduced serum LDL-cholesterol and apolipoprotein B levels, and, furthermore, are protected from diet-induced hypercholesterolemia. (Farese et al., *Proc. Natl. Acad. Sci. U.S.A.*, 1995, 92, 1774-1778).

SUMMARY OF THE INVENTION

In a first aspect, provided herein are methods comprising administering to a subject a pharmaceutical composition comprising an antisense oligonucleotide complementary to a nucleic acid encoding human apolipoprotein B-100, wherein the administering comprises an induction phase, wherein a dose of the antisense oligonucleotide ranging from 100-300 mg is administered once per week for at least 13 weeks, followed by a maintenance phase, wherein a dose of the antisense oligonucleotide ranging from 80-200 mg is administered once per week or once every two weeks for as long as needed, effective, and/or tolerated.

In certain embodiments, the dose administered in the induction phase is a 100 mg dose and the dose administered in the mainteance phase is a 200 mg dose administered once per week. In certain embodiments, the dose administered in the induction phase is a 200 mg dose, and the dose administered in the mainteance phase is a 300 mg dose administered once per week. In certain embodiments, the dose administered in the induction phase is a 100 mg dose and the dose administered in the mainteance phase is a 200 mg dose administered once per week, and wherein the tolerability or the effectiveness of the antisense oligonucleotide are assessed during or at the end of the induction period, or a portion thereof once per week during the maintenance phase. In certain embodiments, the dose administered in the induction phase is a 200 mg dose and the dose administered in the mainteance phase is a 300 mg dose administered once per week, and wherein the tolerability or the effectiveness of the antisense oligonucleotide are assessed during or at the end of the induction period, or a portion thereof.

In certain embodiments, the dose administered in the induction phase is a 100 mg dose and the dose administered in the mainteance phase is a 100 mg dose administered once every two weeks, and wherein the tolerability or the effectiveness of the antisense oligonucleotide are assessed during or at the end of the induction period, or a portion thereof. In certain embodiments, the dose administered in the induction phase is a 200 mg dose and the dose administered in the mainteance phase is a 200 mg dose administered once every two weeks, and wherein the tolerability or the effectiveness of the antisense oligonucleotide are assessed during or at the end of the induction period, or a portion thereof. In certain embodiments, the dose administered in the induction phase is from 100 mg to 200 mg and the dose administered in the maintenance phase is from 200 mg to 300 mg and is administered once per week.

In certain embodiments, said administering comprises parenteral administration. In certain embodiments, said parenteral administration comprises subcutaneous administration. In certain embodiments, each induction dose and each maintenance dose comprises a single injection. In certain embodiments, each induction dose and each maintenance dose independently comprise two or more injections. In certain embodiments, the methods further comprise assessing the tolerability or effectiveness of the antisense oligonucleotide during or at the end of the induction period, or a portion thereof. In certain embodiments, the tolerability and the effectiveness of the antisense oligonucleotide are assessed In certain embodiments, the tolerability of the antisense oligonucleotide is assessed by monitoring a rate of decrease of ApoB concentration in the plasma of said subject. In certain embodiments, the tolerability of the antisense oligonucleotide is assessed by monitoring ApoB concentration in the plasma of said subject. In certain embodiments, the tolerability of the antisense oligonucleotide is assessed by monitoring a rate of decrease of ApoB concentration and ApoB concentration in the plasma of said subject. In certain embodiments, the tolerability of the antisense oligonucleotide is assessed by monitoring ALT concentrations in the liver of the subject. In certain embodiments, the tolerability of the antisense oligonucleotide is assessed by monitoring ANT concentrations in the liver of said subject. In certain embodiments, the tolerability of the antisense oligonucleotide is assessed by monitoring bilirubin concentrations in the plasma of the subject.

In certain embodiments, a rate of decrease in the ApoB concentration greater than about 30 mg/dL*day indicates that the subject is not tolerating administration of the antisense oligonucleotide. In certain embodiments, an ApoB concentration less than about 60 mg/dL indicates that the subject is not tolerating administration of the antisense oligonucleotide. In certain embodiments, a rate of decrease in the ApoB concentration greater than about 30 mg/dL*day and an ApoB concentration less than about 60 mg/dL indicates that the subject is not tolerating administration of the antisense oligonucleotide. In certain embodiments, the dose of antisense oligonucleotide is reduced following an indication that administration of said antisense oligonucleotide is not tolerated. In certain embodiments, the frequency of administration of antisense oligonucleotide is reduced following an indication that administration of said antisense oligonucleotide is not tolerated. In certain embodiments, the dose of antisense oligonucleotide is increased following an indication that administration of said antisense oligonucleotide is tolerated. In certain embodiments, the frequency of administration of antisense oligonucleotide is increased following an indication that administration of said antisense oligonucleotide is tolerated.

In certain embodiments, the effectiveness of the antisense oligonucleotide is assessed by monitoring ApoB, LDL-C, VLDL-C, IDL-C, non-HDL-C, serum triglycerides, liver triglycerides, Lp(a), Ox-LDL-C, or small dense LDL particle concentration in the plasma of said subject. In certain embodiments, a reduction of ApoB, LDL-C, VLDL-C, IDL-C, non-HDL-C, serum triglycerides, liver triglycerides, Lp(a), Ox-LDL-C, or small dense LDL particle concentration indicates that the antisense oligonucleotide is effective. In certain embodiments, the dose of antisense oligonucleotide is reduced following an indication that administration of said antisense oligonucleotide is effective. In certain embodiments, the dose of antisense oligonucleotide is increased following an indication that administration of said antisense oligonucleotide is not effective. In certain embodiments, the frequency of administration of antisense oligonucleotide is reduced following an indication that administration of said antisense oligonucleotide is effective. In certain embodiments, the frequency of administration of antisense oligonucleotide is increased following an indication that administration of said antisense oligonucleotide is not effective.

In certain embodiments, said subject has elevated ApoB prior to said administering. In certain embodiments, said subject has elevated cholesterol prior to said administering. In certain embodiments, said elevated cholesterol is selected from elevated total cholesterol, elevated LDL-cholesterol, elevated VLDL-cholesterol, elevated IDL-cholesterol, or elevated non-HDL cholesterol prior to said administering. In certain embodiments, said subject has elevated Lp(a) prior to said administering. In certain embodiments, said subject has elevated serum triglycerides prior to said administering. In certain embodiments, said subject has elevated liver triglycerides prior to said administering. In certain embodiments, said subject has elevated small dense LDL particles prior to said administering.

In certain embodiments, said subject has hypercholesterolemia. In certain embodiments, said subject has polygenic hypercholesterolemia. In certain embodiments, said subject has familial hypercholesterolemia. In certain embodiments, said subject has homozygous familial hypercholesterolemia. In certain embodiments, said subject has heterozygous familial hypercholesterolemia. In certain embodiments, said subject has mixed dyslipidemia. In certain embodiments, said subject has a history of coronary heart disease.

In certain embodiments, said subject has one or more risk factors for coronary heart disease. In certain embodiments, said one or more risk factors is selected from age, smoking, hypertension, low HDL-cholesterol, and a family history of early coronary heart disease. In certain embodiments, said subject has type II diabetes with dyslipidemia. In certain embodiments, said subject has been treated by a statin. In certain embodiments, said subject failed to meet LDL-cholesterol target on statin therapy. In certain embodiments, said subject did not comply with recommended therapy. In certain embodiments, said subject experienced side effects of stain therapy. In certain embodiments, said subject has low LDL-receptor activity. In certain embodiments, said subject failed to meet LDL-cholesterol target on lipid-lowering therapy prior to said administering.

In certain embodiments, said maintenance phase comprises administering said pharmaceutical composition throughout the lifetime of the subject. In certain embodiments, the duration of said maintenance phase is one year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, or 20 years. In certain embodiments, the duration of said maintenance phase is from one week to twenty years.

In certain embodiments, the induction dose is 100 mg. In certain embodiments, the induction dose is 200 mg. In certain embodiments, the induction dose is 300 mg. In certain embodiments, the maintenance dose is 100 mg. In certain embodiments, the maintenance dose is 200 mg.

In certain embodiments, said administering of said pharmaceutical composition results in antisense oligonucleotide plasma trough levels between 5 and 100 ng/mL. In certain embodiments, said administering of said pharmaceutical composition results in antisense oligonucleotide plasma trough levels between 5 and 50 ng/mL. In certain embodiments, said administering of said pharmaceutical composition results in antisense oligonucleotide plasma trough levels between 10 and 40 ng/mL. In certain embodiments, said administering of said pharmaceutical composition results in antisense oligonucleotide plasma trough levels between 15 and 35 ng/mL. In certain embodiments, said administering of said pharmaceutical composition results in antisense oligonucleotide plasma trough levels between 20 and 30 ng/mL.

In certain embodiments, said administering of said pharmaceutical composition results in ApoB reduction of at least 10%. In certain embodiments, said ApoB reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, said ApoB reduction is between 10% and 80%, between 20% and 70%, between 30% and 60%, or between 30% and 70%.

In certain embodiments, said administering of said pharmaceutical composition results in a LDL-cholesterol reduction of at least 10%. In certain embodiments, said LDL-cholesterol reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, said administering of said pharmaceutical composition results in a VLDL-cholesterol reduction of at least 10%. In certain embodiments, said VLDL-cholesterol reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In certain embodiments, said administering of said pharmaceutical composition results in Lp(a) reduction of at least 10%. In certain embodiments, said Lp(a) reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, said administering of said pharmaceutical composition results in a small LDL-particle reduction of at least 10%. In certain embodiments, said small LDL-particle reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In certain embodiments, said administering of said pharmaceutical composition results in a non-HDL-cholesterol reduction of at least 10%. In certain embodiments, said non-HDL-cholesterol reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In certain embodiments, said administering of said pharmaceutical composition results in reduced coronary heart disease risk in the subject. In certain embodiments, said administering of said pharmaceutical composition slows or stops the progression of atherosclerosis in the subject. In certain embodiments, said administering of said pharmaceutical composition reduces the risk of developing atherosclerosis in the subject. In certain embodiments, said administering of said pharmaceutical composition results in improved cardiovascular outcome the subject. In certain embodiments, said improved cardiovascular outcome is a reduced risk of major cardiovascular adverse events in the subject. In certain embodiments, said improved cardiovascular outcome is improved carotid intimal media thickness. In certain embodiments, said improved cardiovascular outcome is improved atheroma thickness. In certain embodiments, said improved cardiovascular outcome is increased HDL-cholesterol.

In certain embodiments, said administering results in lipid lowering. In certain embodiments, said administering results in reductions in LDL-cholesterol, triglycerides, or small LDL particles, or a combination thereof. In certain embodiments, said administering results in an improved LDL/HDL ratio. In certain embodiments, said administering results in an HDL-cholesterol level increase of at least 10%. In certain embodiments, said HDL-cholesterol level increase is 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, said administering of said pharmaceutical composition results in a liver triglyceride level decrease of at least 10%.

In certain embodiments, said liver triglyceride level decrease is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In certain embodiments, said administering of said pharmaceutical composition results in a hepatic cholesterol ester reduction of at least 10%. In certain embodiments, said reduced hepatic cholesterol ester reduction 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In certain embodiments, the methods further comprise co-administration of said pharmaceutical composition and at least one additional therapy. In certain embodiments, said co-administration is simultaneous. In certain embodiments, said pharmaceutical composition is administered prior to administration of said additional therapy. The method of claim 100, wherein said pharmaceutical composition is administered after administration of said additional therapy. In certain embodiments, the interval between administration of said pharmaceutical composition and said additional therapy is about one hour, about 2 hours, about 3 hours, about 4 hours, about 5 hours, about 6 hours, about 7 hours, about 8 hours, about 9 hours, about 10 hours, about 11 hours, or about 12 hours. In certain embodiments, the interval between administration of said pharmaceutical composition and said additional therapy is about 1 day, about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In certain embodiments, the interval between administration of said pharmaceutical composition and said additional therapy is about 1 month, about 2 months, about 3 months, about 4 months, about 5 months, or about 6 months.

In certain embodiments, the methods further comprise administering a single additional therapy. In certain embodiments, the methods further comprise administering at 2 or more additional therapies. In certain embodiments, said additional therapy is a lipid-lowering therapy. In certain embodiments, said additional lipid-lowering therapy is therapeutic lifestyle change. In certain embodiments, said additional lipid-lowering therapy is an HMG-CoA reductase inhibitor. In certain embodiments, the HMG-CoA reductase inhibitor is selected from atorvastatin, rosuvastatin, or simvastatin. In certain embodiments, said additional lipid-lowering therapy is a cholesterol absorption inhibitor. In certain embodiments, the cholesterol absorption inhibitor is ezetimibe. In certain embodiments, said 2 or more additional therapies comprises an HMG-CoA reductase inhibitor and a cholesterol absorption inhibitor. In certain embodiments, said HMG-CoA reductase inhibitors is simvastatin and said cholesterol absorption inhibitor is ezetimibe. In certain embodiments, said additional lipid-lowering therapy is LDL apheresis. In certain embodiments, said administering of said additional therapy comprises intravenous administration. In certain embodiments, said additional lipid-lowering therapy is an MTP inhibitor.

In certain embodiments, said pharmaceutical composition comprises a pharmaceutically acceptable excipient. In certain embodiments, said pharmaceutically acceptable excipient is saline. In certain embodiments, the dose of the antisense oligonucleotide concentration is administered at a concentration of about 50 mg/ml, about 75 mg/ml, about 100 mg/ml, about 125 mg/ml, about 150 mg/ml, about 175 mg/ml, about 200 mg/ml, about 225 mg/ml, or about 250 mg/ml.

In certain embodiments, the antisense oligonucleotide comprises at least one modified sugar moiety. In certain embodiments, the modified sugar moiety comprises a 2'-methoxyethyl sugar moiety. In certain embodiments, the modified sugar moiety comprises a bicyclic nucleic acid sugar moiety.

In certain embodiments, the antisense oligonucleotide comprises a 2'-deoxynucleotide gap segment positioned between wing segments, wherein each nucleotide of the wing segments comprises a modified sugar moiety. In certain embodiments, each nucleotide of the wing segment comprises a 2'-O-methoxyethyl sugar moiety. In certain embodiments, each nucleotide of the wing segment comprises a bicyclic nucleic acid sugar moiety. In certain embodiments, the gap segment comprises ten nucleotides and each wing segment comprises five nucleotides.

In certain embodiments, at least one internucleoside linkage is a phosphorothioate internucleoside linkage. In certain embodiments, each internucleoside linkage is a phosphorothioate internucleoside linkage.

In certain embodiments, at least one cytosine is a 5-methylcytosine. In certain embodiments, each cytosine is a 5-methylcytosine.

In certain embodiments, the antisense oligonucleotide is at least 90% complementary to a nucleic acid encoding human ApoB. In certain embodiments, the antisense oligonucleotide is at least 95% complementary to a nucleic acid encoding human ApoB. In certain embodiments, the antisense oligonucleotide is 100% complementary to a nucleic acid encoding human ApoB.

In certain embodiments, the nucleic acid encoding human ApoB comprises a sequence identified by Accession number NM_000384.1 (SEQ ID NO: 1).

In certain embodiments, the antisense oligonucleotide comprises 12 to 30 nucleotides. In certain embodiments, the antisense oligonucleotide comprises 15 to 25 nucleotides. In certain embodiments, the antisense oligonucleotide comprises 17 to 23 nucleotides. In certain embodiments, the antisense oligonucleotide comprises 18 to 22 nucleotides. In certain embodiments, the antisense oligonucleotide comprises 19 to 21 nucleotides. In certain embodiments, the antisense oligonucleotide comprises 20 nucleotides.

In certain embodiments, the antisense oligonucleotide is ISIS 301012.

In certain embodiments of the present invention are methods comprising administering to a subject a pharmaceutical composition comprising an antisense oligonucleotide complementary to a nucleic acid encoding human ApoB, wherein the administering comprises an induction phase comprising at least one induction dose and a maintenance phase comprising at least one maintenance dose, wherein the duration of the induction phase is greater than five weeks.

In certain embodiments of the present invention are methods comprising administering to a subject a pharmaceutical composition comprising an antisense oligonucleotide complementary to a nucleic acid encoding human ApoB, wherein the administering comprises an induction phase comprising at least one induction dose and a maintenance phase comprising at least one maintenance dose, wherein an induction dose is less than a maintenance dose.

In certain embodiments of the present invention are methods comprising administering to a subject a pharmaceutical composition comprising an antisense oligonucleotide complementary to a nucleic acid encoding human ApoB, wherein the administering comprises an induction phase comprising at least one induction dose.

In certain embodiments of the present invention are methods comprising administering to a subject having familial hypercholesterolemia a pharmaceutical composition comprising an antisense oligonucleotide complementary to a nucleic acid encoding human ApoB, wherein the administering comprises an induction phase comprising at least one induction dose and a maintenance phase comprising at least one maintenance dose, wherein the induction phase is at least 8 weeks.

In certain embodiments of the present invention are methods comprising administering to a subject a pharmaceutical composition comprising an antisense oligonucleotide complementary to a nucleic acid encoding human apolipoprotein B-100, wherein the administering comprises a maintenance phase comprising at least one maintenance dose.

FIG. 1 shows the predicted LDL-C (% change from baseline) after dosing at 200, 400, or 800 mg once monthly for 12 months.

Figure 2:
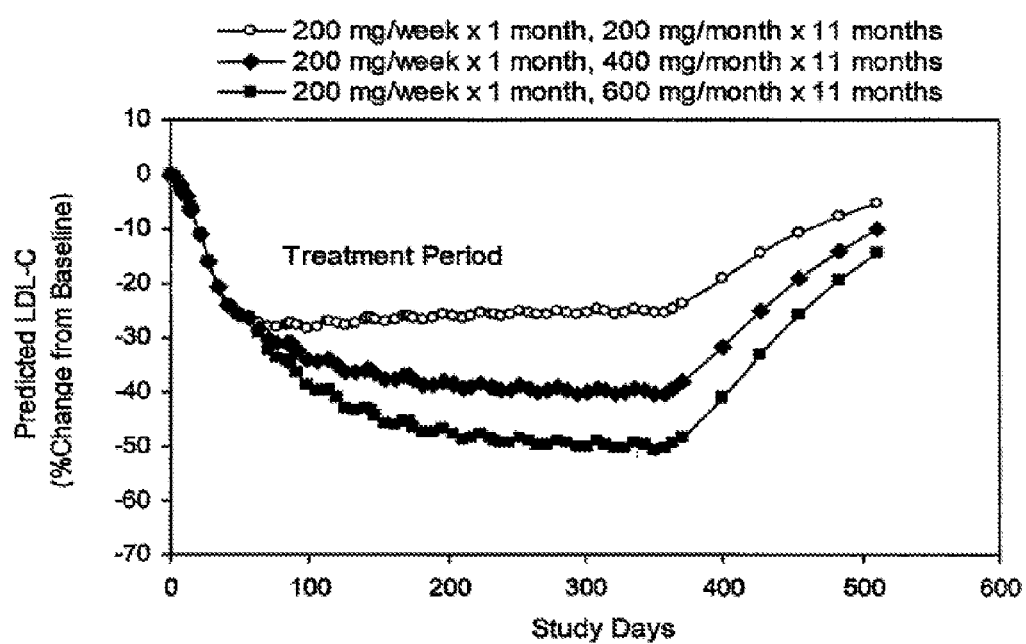

FIG. 2 shows the predicted LDL-C (% change from baseline) after dosing at 200 mg/wk for 1 month then 200, 400, or 600 mg once monthly for 11 months.

Figure 3:
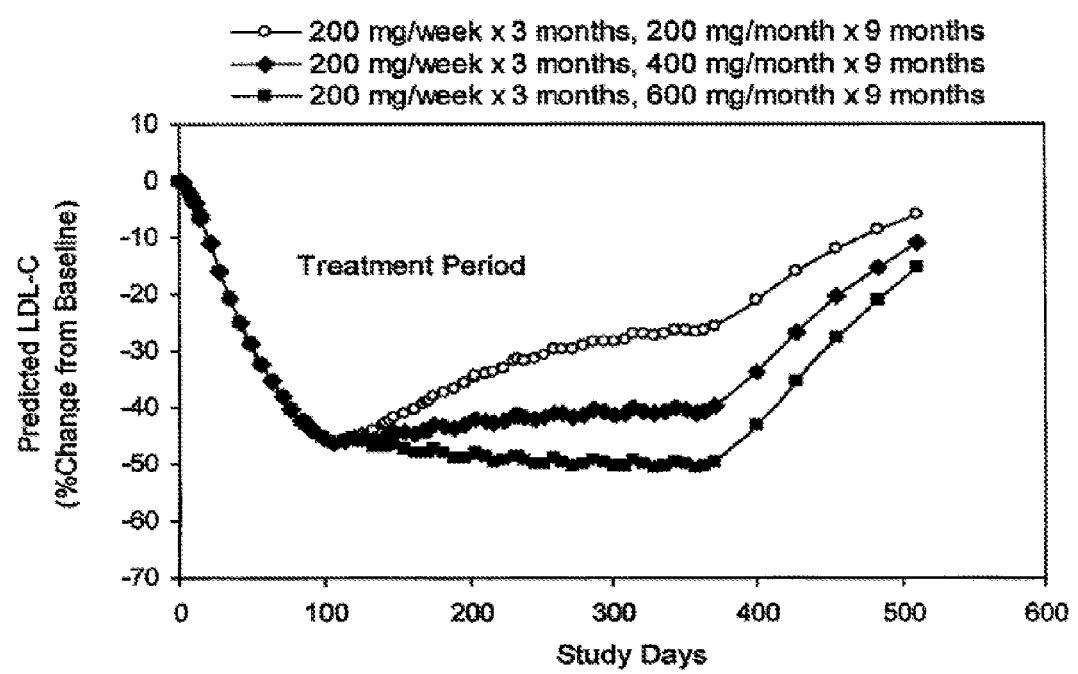

FIG. 3 shows the predicted LDL-C (% change from baseline) after dosing at 200 mg/wk for 3 month then 200, 400, or 600 mg once monthly for 9 months.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose. U.S. patent application Ser. Nos. 10/712,795 and 10/200,710 are hereby expressly incorporated by reference in their entirety for any purpose.

A. DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, chemical analysis, pharmaceutical preparation, formulation and delivery, and treatment of subjects. Certain such techniques and procedures may be found for example in "Remington's Pharmaceutical Sciences," Mack Publishing Co., Easton, Pa., 18th edition, 1990 and [other important formulations and drug delivery references] which is hereby incorporated by reference for any purpose.

As used herein, a "pharmaceutical composition" means a mixture of substances suitable for administering to a subject. For example, a pharmaceutical composition may comprise an antisense oligonucleotide and a sterile aqueous solution.

As used herein, an "antisense oligonucleotide" means a single-stranded oligonucleotide having a nucleobase sequence that permits hybridization to a corresponding region of a target nucleic acid. Such an antisense oligonucleotide is "targeted to" the nucleic acid.

As used herein, "complementarity" means the capacity for pairing between nucleobases of a first nucleic acid and a second nucleic acid.

As used herein, "fully complementary" means each nucleobase of an oligonucleotide is capable of precise base pairing with the corresponding nucleobases of a target nucleic acid.

As used herein, "antisense inhibition" means reduction of target nucleic acid levels in the presence of an olignucleotide complementary to a target nucleic acid compared to target nucleic acid levels in the absence of the oligonucleotide.

As used herein, the terms "target nucleic acid," "target RNA," "target RNA transcript" and "nucleic acid target" all mean any nucleic acid capable of being targeted by antisense oligonucleotides. As used herein, the terms "ApoB target nucleic acid" and "nucleic acid encoding ApoB" encompass nucleic acid, including, for example, DNA (including, for example, cDNA), RNA (including, for example pre-mRNA, and mRNA) transcribed from DNA encoding ApoB, and also cDNA derived from such RNA. In one embodiment, an ApoB target nucleic acid is the sequence of GENBANK® Accession No. NM_000384.1, first deposited with GENBANK® on Mar. 24, 1999.

As used herein, "a nucleic acid encoding human ApoB" means DNA encoding ApoB, or RNA transcribed from DNA encoding ApoB.

As used herein, "administering" means providing a pharmaceutical agent to a subject, and includes, but is not limited to administering by a medical professional and self-administering.

As used herein, a "subject" means a human or non-human animal selected for treatment or therapy.

As used herein, "induction phase" means a dosing phase during which administration is initiated and steady state concentrations of active pharmaceutical agent are achieved in a target tissue. For example, an induction phase is a dosing phase during which steady state concentrations of antisense oligonucleotide are achieved in liver.

As used herein, "maintenance phase" means a dosing phase after target tissue steady state concentrations of drug have been achieved.

As used herein, "duration" means the period of time during which an activity or event continues. For example, the duration of an induction phase is the period of time during which induction doses are administered. For example, the duration of a maintenance phase is the period of time during which maintenance doses are administered.

As used herein, "parenteral administration," means administration through injection or infusion. Parenteral administration includes, but is not limited to, subcutaneous administration, intravenous administration, or intramuscular administration.

As used herein, "subcutaneous administration" means administration just below the skin. As used herein, "intravenous administration" means administration into a vein.

As used herein, "maintenance dose" means a dose administered at a single administration during the maintenance phase. As used herein, "induction dose" means a dose administered at a single administration during the induction phase.

As used herein, a "dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in a subject.

As used herein, a "dosage unit" means a form in which a pharmaceutical agent is provided. In certain embodiments, a dosage unit is a vial containing lyophilized ISIS 301012. In certain embodiments, a dosage unit is a vial containing reconstituted ISIS 301012.

As used herein, a "dosing regimen" is a combination of doses designed to achieve one or more desired effects. In certain embodiments, a dose regimen is designed to provide a therapeutic effect quickly. In certain embodiments a dose regimen is designed to reduce and undesired side effect, for example, liver toxicity.

As used herein, a "pharmaceutical agent" means a substance provides a therapeutic benefit when administered to a subject. For example, in certain embodiments, an antisense oligonucleotide targeted to ApoB is pharmaceutical agent.

As used herein, "active pharmaceutical ingredient" means the substance in a pharmaceutical composition that provides a desired effect. For example, ISIS 301012 is the active pharmaceutical ingredient in a pharmaceutical composition comprising ISIS 301012 and saline.

As used herein, "ApoB" means apolipoprotein B-100 protein. Concentration of ApoB in serum (or plasma) is typically quantified in mg/dL or nmol/L. "Serum ApoB" and "plasma ApoB" mean ApoB in the serum and plasma, respectively.

As used herein, "low density lipoprotein-cholesterol (LDL-C)" means cholesterol associated with low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

As used herein, "very low density lipoprotein-cholesterol (VLDL-C)" means cholesterol associated with very low density lipoprotein particles. Concentration of VLDL-C in serum (or plasma) is typically quantified in mg/dL or nmol/L. "Serum VLDL-C" and "plasma VLDL-C" mean VLDL-C in the serum or plasma, respectively.

As used herein, "intermediate low density lipoprotein-cholesterol (IDL-C)" means cholesterol associated with intermediate density lipoprotein. Concentration of IDL-C in serum (or plasma) is typically quantified in mg/mL or nmol/L. "Serum IDL-C" and "plasma IDL-C" mean IDL-C in the serum or plasma, respectively.

As used herein, "non-high density lipoprotein-cholesterol (Non-HDL-C)" means cholesterol associated with lipoproteins other than high density lipoproteins, and includes, without limitation, LDL-C, VLDL-C, and IDL-C.

As used herein, "high density lipoprotein-C (HDL-C)" means cholesterol associated with high density lipoprotein particles. Concentration of HDL-C in serum (or plasma) is typically quantified in mg/dL or nmol/L. "Serum HDL-C" and "plasma HDL-C" mean HDL-C in the serum and plasma, respectively.

As used herein, "total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

As used herein, "lipoprotein(a)" or "Lp(a)" means a lipoprotein particle that is comprised of LDL-C, an apolipoprotein(a) particle, and an apolipoproteinB-100 particle.

As used herein, "ApoA1" is apolipoprotein-A1 protein in serum. Concentration of ApoA1 in serum is typically quantified in mg/dL or nmol/L.

As used herein, "ApoB:ApoA1 ratio" is the ratio of ApoB concentration to ApoA1 concentration.

As used herein, "ApoB-containing lipoprotein" means any lipoprotein that has apolipoprotein B as its protein component, and is understood to include LDL, VLDL, IDL, and lipoprotein(a).

As used herein, "small dense LDL particles" means a subclass of LDL particles characterized by a smaller, denser size compared to other LDL particles.

As used herein, "triglycerides" means lipids that are the triesters of glycerol. "Serum triglycerides" mean triglycerides present in serum. "Liver triglycerides" mean triglycerides present in liver tissue.

As used herein, "serum lipids" include, but are not limited to, serum cholesterol and serum triglycerides.

As used herein, "cholesteryl ester content" means the amount of cholesteryl ester present in liver tissue. In certain embodiments, serum cholesteryl ester concentration is used as an indicator of hepatic cholesteryl ester content.

As used herein, "elevated total cholesterol" means total cholesterol at a concentration in a subject at which lipid-lowering therapy is recommended, and includes, without limitation, elevated LDL-C", "elevated VLDL-C," "elevated IDL-C," and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

As used herein, "elevated triglyceride" means concentrations of triglyceride in the serum or liver at which lipid-lowering therapy is recommended, and includes "elevated serum triglyceride" and "elevated liver triglyceride." In certain embodiments, serum triglyceride concentration of 150-199 mg/dL, 200-499 mg/dL, and greater than or equal to 500 mg/dL is considered borderline high, high, and very high, respectively.

As used herein, "elevated small dense LDL particles" means a concentration of small dense LDL particles in a subject at which lipid-lowering therapy is recommended.

As used herein, "elevated lipoprotein(a)" means a concentration of lipoprotein(a) in a subject at which lipid-lowering therapy is recommended.

As used herein, "low HDL-C" means a concentration of HDL-C in a subject at which lipid-lowering therapy is recommended. In certain embodiments lipid-lowering therapy is recommended when low HDL-C is accompanied by elevations in non-HDL-C and/or elevations in triglyceride. In certain embodiments, HDL-C concentrations of less than 40 mg/dL are considered low. In certain embodiments, HDL-C concentrations of less than 50 mg/dL are considered low.

As used herein, "$C_{trough}$" or "plasma trough concentration" means a minimum plasma concentration when plasma pharmaceutical agent concentrations are in equilibrium with target tissue pharmaceutical agent concentrations. For example, in certain embodiments, a plasma trough concentration of ISIS 301012 is achieved when plasma ISIS 301012 concentrations are in equilibrium with liver tissue ISIS 301012 concentrations.

As used herein, "$AUC_{trough}$" or "plasma trough AUC" means the area under the concentration-time curve at a time when plasma pharmaceutical agent concentrations are in equilibrium with target tissue pharmaceutical agent concentrations.

As used herein, "LDL/HDL ratio" means the ratio of LDL-C to HDL-C.

As used herein, "Oxidized-LDL" or "Ox-LDL-C" means LDL-C that is oxidized following exposure to free radicals.

As used herein, "hypercholesterolemia" means a condition characterized by elevated serum cholesterol. In certain embodiments, hypercholesterolemia includes, but is not limited to, polygenic hypercholesterolemia, heterozygous familial hypercholesterolemia, and a homozgygous familial hypercholesterolemia.

As used herein, "hyperlipidemia" means a condition characterized by elevated serum lipids.

As used herein, "hypertriglyceridemia" means a condition characterized by elevated triglyceride levels.

As used herein, "non-familial hypercholesterolemia" means a condition characterized by elevated cholesterol that is not the result of a single gene mutation.

As used herein, "polygenic hypercholesterolemia" means a condition characterized by elevated cholesterol that results from the influence of a variety of genetic factors. In certain embodiments, polygenic hypercholesterolemia may be exacerbated by dietary intake of lipids.

As used herein, "familial hypercholesterolemia (FH)" means an autosomal dominant metabolic disorder characterized by a mutation in the LDL-receptor (LDL-R) gene, markedly elevated LDL-C and premature onset of atherosclerosis. A diagnosis of familial hypercholesterolemia is made when a subject meets one or more of the following criteria: genetic testing confirming 2 mutated LDL-receptor genes; genetic testing confirming one mutated LDL-receptor gene; document history of untreated serum LDL-cholesterol greater than 500 mg/dL; tendinous and/or cutaneous xanthoma prior to age 10 years; or, both parents have documented elevated serum LDL-cholesterol prior to lipid-lowering therapy consistent with heterozygous familial hypercholesterolemia.

As used herein, "homozygous familial hypercholesterolemia" or "HoFH" means a condition characterized by a mutation in both maternal and paternal LDL-R genes.

As used herein, "Heterozygous familial hypercholesterolemia" or "HeFH" is a condition characterized by a mutation in either the maternal or paternal LDL-R gene.

As used herein, "mixed dyslipidemia" means a condition characterized by elevated serum cholesterol and elevated serum triglycerides.

As used herein, "diabetic dyslipidemia" or "Type II diabetes with dyslipidemia" means a condition characterized by Type II diabetes, reduced HDL-C, elevated serum triglycerides, and elevated small, dense LDL particles.

As used herein, "CHD risk equivalents," means indicators of clinical atherosclerotic disease that confer a high risk for coronary heart disease, and include clinical coronary heart disease, symptomatic carotid artery disease, peripheral arterial disease, and/or abdominal aortic aneurysm.

As used herein, "Major risk factors" that contribute to a high risk for coronary heart disease include cigarette smoking, hypertension, low HDL-C, family history of coronary heart disease, and age.

As used herein, "CHD risk factors" include CHD risk equivalents and major risk factors.

As used herein, "coronary heart disease (CHD)" means a narrowing of the small blood vessels that supply blood and oxygen to the heart, which is often a result of atherosclerosis.

As used herein, "reduced coronary heart disease risk" means a reduction in the likelihood that a subject will develop coronary heart disease.

As used herein, "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

As used herein, "history of coronary heart disease" means the occurrence of clinically evident coronary heart disease in the medical history of a subject or a subject's family member.

As used herein, "early onset coronary heart disease" means a diagnosis of coronary heart disease prior to age 50.

As used herein, "statin intolerant subject" means a subject who as a result of statin therapy experiences one or more of creatine kinase increases, liver function test abnormalities, muscle aches, or central nervous system side effects.

As used herein, "efficacy" means the ability to produce a desired effect. For example, efficacy of a lipid-lowering therapy may be reduction in the concentration of one or more of LDL-C, VLDL-C, non-HDL-C, ApoB, lipoprotein(a), or triglycerides.

As used herein, "acceptable safety profile" means a pattern of side effects that is within clinically acceptable limits.

As used herein, "side effects" means physiological responses attributable to a treatment other than desired effects. In the present context, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

As used herein, "injection site reaction" means inflammation or abnormal redness of skin at a site of injection in a subject.

As used herein, "subject compliance" means adherence to a recommended or prescribed therapy by a subject.

As used herein, "lipid-lowering therapy" means a therapeutic regimen provided to a subject to reduce one or more lipids in a subject. In certain embodiments, a lipid-lowering therapy is provide to reduce one or more of ApoB, total cholesterol, LDL-C, VLDL-C, IDL-C, non-HDL-C, triglycerides, small dense LDL particles, and Lp(a) in a subject.

As used herein, "lipid-lowering agent" means a pharmaceutical agent provided to a subject to achieve a lowering of lipids in the subject. For example, in certain embodiments, a lipid-lowering agent is provided to a subject to reduce one or more of ApoB, LDL-C, total cholesterol, and triglyerides.

As used herein, "LDL-C target" is an LDL-C level that is desired following lipid-lowering therapy.

As used herein, "comply" as used herein means the adherence to a recommended therapy by a subject.

As used herein, "recommended therapy" means a therapeutic regimen recommended by a medical professional for the treatment, amelioration, or prevention of a disease.

As used herein, "low LDL-receptor activity" means LDL-receptor activity that is not sufficiently high to maintain clinically acceptable levels of LDL-C in the bloodstream.

As used herein, "cardiovascular outcome" means the occurance of major adverse cardiovascular events.

As used herein, "improved cardiovascular outcome" means a reduction in the occurance of major adverse cardiovascular events, or the risk thereof. Examples of major adverse cardiovascular events include, without limitation, death, reinfarction, stroke, cardiogenic shock, pulmonary edema, cardiac arrest, and atrial dysrhythmia.

As used herein, "surrogate markers of cardiovascular outcome" means indirect indicators of cardiovascular events, or the risk thereof. For example, surrogate markers of cardiovascular outcome include carotid intimal media thickness (CIMT). Another example of a surrogate marker of cardiovascular outcome includes atheroma size. Atheroma size may be determined by intravascular ultrasound (IVUS).

As used herein, "increased HDL-C" means an increase in serum HDL-C in a subject over time.

As used herein, "lipid-lowering" means a reduction in one or more serum lipids in a subject over time.

As used herein, "co-administration" means administration of two or more pharmaceutical agents to a subject. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

As used herein, "therapeutic lifestyle change" means dietary and lifestyle changes intended to lower cholesterol and reduce the risk of developing heart disease, and includes recommendations for dietary intake of total daily calories, total fat, saturated fat, polyunsaturated fat, monounsaturated fat, carbohydrate, protein, cholesterol, insoluble fiber, as well as recommendations for physical activity.

As used herein, "statin" means a pharmaceutical agent that inhibits the activity of HMG-CoA reductase.

As used herein, "HMG-CoA reductase inhibitor" means a pharmaceutical agent that acts through the inhibition of the enzyme HMG-CoA reductase.

As used herein, "cholesterol absorption inhibitor" means a pharmaceutical agent that inhibits the absorption of exogenous cholesterol obtained from diet.

As used herein, "LDL apheresis" means a form of apheresis by which LDL-C is removed from blood. Typically, a subject's blood is removed from a vein, and separated into red cells and plasma. LDL-C is filtered out of the plasma prior to return of the plasma and red blood cells to the subject.

As used herein, "MTP inhibitor" means a pharmaceutical agent that inhibits the enzyme microsomal triglyceride transfer protein.

As used herein, "nucleoside" means a base-sugar combination.

As used herein, "nucleobase" means a heterocyclic base moiety.

As used herein, "nucleotide" means a nucleoside having a phosphate group covalently linked to the sugar portion of the nucleoside.

As used herein "internucleoside linkage" means a covalent linkage between adjacent nucleosides As used herein "naturally occurring internucleoside linkage" means a 3' to 5' phosphodiester linkage.

As used herein "oligonucleotide" means a polymer of linked nucleotides, each of which can be, independently, modified or unmodified.

As used herein "oligonucleoside" means an oligonucleotide in which the internucleoside linkages do not contain a phosphorus atom.

As used herein "unmodified" nucleobases mean the purine bases adenine (A) and guanine (G), and the pyrimidine bases thymine (T), cytosine (C) and uracil (U).

As used herein "modified sugar moiety" means a sugar moiety having a substitution and/or any change from a natural sugar moiety.

As used herein, a "natural sugar moiety" means a sugar moiety found in DNA (2'-H) or RNA (2'-OH).

As used herein a "2'-O-methoxyethyl sugar moiety" means a 2'-substituted furosyl ring having a 2'-O(CH$_2$)$_2$—OCH$_3$ (2'-O-methoxyethyl or 2'-MOE) substituent group.

As used herein, "2'-O-methoxyethyl nucleotide" means a nucleotide comprising a 2'-β-methoxyethyl modified sugar moiety.

As used herein "bicyclic nucleic acid sugar moiety" means a furosyl ring modified by the bridging of two non-geminal ring atoms.

As used herein "wing segment" means a plurality of nucleosides modified to impart to an oligonucleotide properties such as enhanced inhibitory activity, increased binding affinity for a target nucleic acid, or resistance to degradation by in vivo nucleases.

As used herein "gap segment" means a plurality of nucleotides that supports cleavage by the endonuclease RNaseH.

As used herein "ISIS 301012" means a lipid-lowering agent that is an antisense oligonucleotide having the sequence "GCCTCAGTCTGCTTCGCACC" (SEQ ID NO: 2), where each internucleoside linkage is a phosphorothioate internucleoside linkage, each cytosine is a 5-methylcytosine, nucleotides 6-15 are 2'-deoxynucleotides, and nucleotides 1-5 and 16-20 are 2'-O-methoxyethyl nucleotides. ISIS 301012 is complementary to nucleotides 3249-3268 of the sequence with GENBANK Accession No. NM_000384.1.

As used herein "Metabolic syndrome" means defined as a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL As used herein, a "therapeutically effective amount" means an amount of a pharmaceutical agent that provides a therapeutic benefit to a subject. For example, a therapeutically effective amount of an antisense oligonucleotide complementary to a nucleic acid encoding human apoB is an amount that results in reduced LDL-C.

B. CERTAIN PHARMACEUTICAL COMPOSITIONS

In certain embodiments, the present invention provides pharmaceutical compositions comprising one or more different oligonucleotides. In certain such embodiments, those pharmaceutical compositions comprise an antisense oligonucleotide complementary to a nucleic acid encoding human apoB. In certain embodiments, such pharmaceutical compositions comprise ISIS 301012. ISIS 301012 is a pharmaceutical agent that, when administered to a subject, results in dose-dependent reductions of ApoB, ApoB-containing lipoproteins, including but not limited to LDL-C, triglycerides, and Lp(a). ISIS 301012 results in efficacy when administered alone, and also results in efficacy when In certain embodiments, pharmaceutical compositions comprise an oligonucleotide having complementary to a target nucleic acid. In certain such embodiments, a sufficient number of nucleobases of the oligonucleotide can undergo hydrogen bonding with corresponding nucleobases in a target nucleic acid such that a desired effect occurs. In certain such embodiments, a desired effect is antisense inhibition of a target nucleic acid. In certain such embodiments, a desired effect is antisense inhibition of apoB. In certain such embodiments, least 70%, at least 75%, at least 80%, at least 85%, at least 90%, at least 95%, at least 96%, at least 97%, at least 98% or at least 99% of the nucleobases of an oligonucleotide can undergo hydrogen bonding with a corresponding nucleobase of a target nucleic acid. In certain such embodiments, 100% of the nucleobases of an oligonucleotide can undergo hydrogen bonding with a corresponding nucleobase of a target nucleic acid. In these embodiments, oligonucleotides are fully complementary (i.e, 100% complementary) to a target nucleic acid. In certain such embodiments, oligonucleotides are fully complementary to a nucleic acid encoding ApoB.

In certain embodiments, a nucleic acid encoding human ApoB is ApoB mRNA. In certain embodiments, such ApoB mRNA may or may not include some or all exons.

In certain embodiments, oligonucleotides are 12 to 30 nucleotides in length, i.e., the oligonucleotides are from 12 to 30 linked nucleotides. In certain such embodiments, oligonucleotides are 15 to 25 nucleotides in length. In certain such embodiments, oligonucleotides are 17 to 23 nucleotides in length. In certain such embodiments, oligonucleotides are 18 to 22 nucleotides in length. In certain such embodiments, oligonucleotides are 19 to 21 nucleotides in length. In certain such embodiments, oligonucleotides are 20 nucleotides in length.

In certain embodiments, oligonucleotides comprise a percent identity to a particular nucleotide sequence. An oligonucleotide has identity to another oligonucleotide if the nucleobases of each oligonucleotide have the same nucleobase pairing ability. In certain such embodiments, an oligonucleotide has 90% identity to another oligonucleotide. In certain such embodiments, an oligonucleotide has 95% identity to another oligonucleotide. In certain such embodiments, an oligonucleotide has 100% identity to another oligonucleotide. In certain such embodiments, the identity is over the full-length of the oligonucleotide. In certain such embodiments, the identity is to a portion of an oligonucleotide.

In certain embodiments, oligonucleotides comprise chemical modifications. In certain such embodiments, modifications to oligonucleotides encompass substitutions or changes to internucleoside linkages, sugar moieties, or nucleobases. Modified oligonucleotides are often preferred over native forms because of desirable properties such as, for example, enhanced cellular uptake, enhanced affinity for nucleic acid target, increased stability in the presence of nucleases, or increased inhibitory activity.

In certain embodiments, chemically modified nucleosides may also be employed to increase the binding affinity of a shortened or truncated antisense oligonucleotide for its target nucleic acid.

In certain embodiments, oligonucleotides comprise one or more modified, i.e. non-naturally occurring, internucleoside linkages. In certain such embodiments, oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, oligonucleotides comprise one or more nucleotides comprising modified sugar moieties. In certain such embodiments, the furanosyl sugar ring of a nucleoside is modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C($R_1$)($R_2$) for the ring oxygen at the 4'-position. In certain such embodiments, modified sugars include, but are not limited to: substituted sugars, especially 2'-substituted sugars having a 2'-F, 2'-OCH$_2$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=2. Methods for the preparations of modified sugars are well known to those skilled in the art.

In certain embodiments, oligonucleotides comprise one or more nucleotides comprising modified nucleobases. In such embodiments, nucleobases are modified so as to maintain hydrogen bonding. In certain such embodiments, modified nucleobases include, but are not limited to, 5-methylcytosine (5-meC). Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

In certain embodiments, pharmaceutical compositions of the present invention comprise one or more oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulosem and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation.

Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, a pharmaceutical composition of the present invention comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more oligonucleotides of the present invention is formulated as a prodrug. In certain embodiments, upon in vivo administration, a prodrug is chemically converted to the biologically, pharmaceutically or therapeutically more active form of the oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In certain embodiments, a pharmaceutical composition comprising one or more pharmaceutical agents of the present invention is useful for treating a conditions or disorders in a mammalian, and particularly in a human, subject. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition of the present invention is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain embodiments, a pharmaceutical composition is comprises a dose of oligonucleotide selected from 50 mg, 100 mg, 150 mg, 200 mg, 250 mg, 300 mg, and 400 mg.

In a further aspect, a pharmaceutical agent is sterile lyophilized oligonucleotide that is reconstituted with a suitable diluent, e.g., sterile water for injection. The reconstituted product is administered as a subcutaneous injection or as an intravenous infusion after dilution into saline. The lyophilized drug product consists of the oligonucleotide which has been prepared in water for injection, adjusted to pH 7.0-9.0 with acid or base during preparation, and then lyophilized. The lyophilized oligonucleotide may be 25-800 mg of the oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal. In one embodiment, the lyophilized pharmaceutical agent comprises ISIS 301012.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

C. CERTAIN DOSING REGIMENS

In certain embodiments, pharmaceutical compositions are administered according to a dosing regimen. In certain such embodiments, the dosing regimen comprises an induction phase and a maintenance phase.

In certain embodiments, the induction phase includes one, two, three, four, five, six, seven, eight, nine, ten, eleven, twelve, thirteen, fourteen, fifteen, sixteen, seventeen, eighteen, nineteen, twenty, or more than twenty doses.

In certain embodiments, the induction phase lasts from one day to six months. In certain embodiments an induction phase lasts from one week to five months as measured from administration of the first dose of the induction phase to administration of the first dose of the maintenance phase. In certain embodiments an induction phase lasts from one week to five months as measured from administration of the first dose of the induction phase to administration of the first dose of the maintenance phase. In certain embodiments an induction phase lasts from two weeks to five months as measured from administration of the first dose of the induction phase to administration of the first dose of the maintenance phase. In certain embodiments an induction phase lasts from three weeks to four months as measured from administration of the first dose of the induction phase to administration of the first dose of the maintenance phase. In certain embodiments an induction phase lasts from five weeks to three months as measured from administration of the first dose of the induction phase to administration of the first dose of the maintenance phase. In certain embodiments an induction phase lasts five weeks as measured from administration of the first dose of the induction phase to administration of the first dose of the maintenance phase. In certain embodiments an induction phase lasts six weeks as measured from administration of the first dose of the induction phase to administration of the first dose of the maintenance phase. In certain embodiments an induction phase lasts seven weeks as measured from administration of the first dose of the induction phase to administration of the first dose of the maintenance phase. In certain embodiments an induction phase lasts eight weeks as measured from administration of the first dose of the induction phase to administration of the first dose of the maintenance phase. In certain embodiments an induction phase lasts nine weeks as measured from administration of the first dose of the induction phase to administration of the first dose of the maintenance phase. In certain embodiments an induction phase lasts ten weeks as measured from administration of the first dose of the induction phase to administration of the first dose of the maintenance phase. In certain embodiments an induction phase lasts eleven weeks as measured from administration of the first dose of the induction phase to administration of the first dose of the maintenance phase. In certain embodiments an induction phase lasts twelve weeks as measured from administration of the first dose of the induction phase to administration of the first dose of the maintenance phase. In certain embodiments an induction phase lasts thirteen weeks as measured from administration of the first dose of the induction phase to administration of the first dose of the maintenance phase. In certain embodiments an induction phase lasts fourteen weeks as measured from administration of the first dose of the induction phase to administration of the first dose of the maintenance phase. In certain embodiments an induction phase lasts fifteen weeks as measured from administration of the first dose of the induction phase to administration of the first dose of the maintenance phase. In certain embodiments an induction phase lasts sixteen weeks as measured from administration of the first dose of the induction phase to administration of the first dose of the maintenance phase. In certain embodiments an induction phase lasts seventeen weeks as measured from administration of the first dose of the induction phase to administration of the first dose of the maintenance phase. In certain embodiments an induction phase lasts eighteen weeks as measured from administration of the first dose of the induction phase to administration of the first dose of the maintenance phase. In certain embodiments an induction phase lasts nineteen weeks as measured from administration of the first dose of the induction phase to administration of the first dose of the maintenance phase. In certain embodiments an induction phase lasts twenty weeks as measured from administration of the first dose of the induction phase to administration of the first dose of the maintenance phase. In certain embodiments an induction phase lasts twenty-one weeks as measured from administration of the first dose of the induction phase to administration of the first dose of the maintenance phase. In certain embodiments an induction phase lasts twenty-two weeks as measured from administration of the first dose of the induction phase to administration of the first dose of the maintenance phase. In certain embodiments an induction phase lasts twenty-three weeks as measured from administration of the first dose of the induction phase to administration of the first dose of the maintenance phase. In certain embodiments an induction phase lasts twenty-four weeks as measured from administration of the first dose of the induction phase to administration of the first dose of the maintenance phase. In certain embodiments an induction phase lasts twenty-five weeks as measured from administration of the first dose of the induction phase to administration of the first dose of the maintenance phase. In certain such embodiments, the doses administered during the induction phase are lower than the doses administered during the maintenance phase.

In certain embodiments, the dose administered during the induction phase is lower than the dose administered during the maintenance phase to avoid undesired side effects. In certain embodiments, the undesired side effect is liver toxicity. In certain such embodiments, the undesired side effect is increased ALT. In certain such embodiments, the lower induction dose provides time for lipid metabolism in the liver to compensate for the decreased production of ApoB. In certain such embodiments, mild increases in ALT reflect rapid lipid-lowering activity.

In certain embodiments where the induction phase includes more than one dose, the doses administered during the induction phase are all the same amount as one another. In certain embodiments, the doses administered during the induction phase are not all the same amount. In certain such embodiments, the doses increase over time. In certain embodiments, the doses decrease over time.

In certain embodiments, an induction dose is administered by parenteral administration. In certain such embodiments, the parenteral administration is subcutaneous administration. In certain such embodiments, the parenteral administration is intravenous infusion.

In certain embodiments, the doses during the induction phase are selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, the doses during the induction phase are selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain such embodiments, the doses during the induction phase are selected from 100 mg, 125 mg, 150 mg, 175 mg, 200 mg, 225 mg, 250 mg, 275 mg, 300 mg, 325 mg, 350 mg, 375 mg, and 400 mg. In certain such embodiments, the doses during the induction phase are selected from 100 mg, 125 mg, 150 mg, 175 mg, 200 mg, 225 mg, and 250 mg. In certain embodiments, the dose administered during the induction phase is 100 mg. In certain embodiments, the dose administered during the induction phase is 125 mg. In certain embodiments the dose administered during the induction phase is 150 mg. In certain embodiments the dose administered during the induction phase is 175 mg. In certain embodiments the dose administered during the induction phase is 200 mg. In certain embodiments the dose administered during the induction phase is 225 mg. In certain embodiments the dose administered during the induction phase is 250 mg. In certain embodiments the dose administered during the induction phase is 300 mg. In certain embodiments the dose administered during the induction phase is 325 mg. In certain embodiments the dose administered during the induction phase is 350 mg. In certain embodiments the dose administered during the induction phase is 375 mg. In certain embodiments the dose administered during the induction phase is 400 mg.

In certain embodiments, where subcutaneous administration is desired, an induction dose may be administered in two or more subcutaneous injections. In certain such embodiments, when the desired induction dose requires a volume not easily accommodated by a single injection, two or more subcutaneous injections may be used to achieve the desired induction dose. In certain such embodiments, two or more subcutaneous injections may be used to administer the desired induction dose and minimize or eliminate an injection site reaction in a subject.

In certain embodiments, dose, dose frequency, and duration of the induction phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent at an amount sufficient to achieve a desired effect. In certain of such embodiments the plasma concentration is maintained above the minimal effective concentration (MEC). In certain embodiments, pharmaceutical compositions of the present invention are administered with a dosage regimen designed to maintain a concentration above the MEC for 10-90% of the time, between 30-90% of the time, or between 50-90% of the time.

In certain embodiments, doses, dose frequency, and duration of the induction phase may be selected to achieve a desired plasma trough concentration of a pharmaceutical composition. In certain such embodiments, the pharmaceutical composition is an oligonucleotide. In certain such embodiments, the desired plasma trough concentration is from 5-100 ng/mL. In certain such embodiments, the desired plasma trough concentration is from 5-50 ng/mL. In certain such embodiments, the desired plasma trough concentration is from 10-40 ng/mL. In certain such embodiments, the desired plasma trough concentration is from 15-35 ng/mL. In certain such embodiments, the desired plasma trough concentration is from 20-30 ng/mL.

In certain embodiments, dose, dose frequency, and duration of the induction phase may be selected to achieve a desired effect within five to thirteen weeks. In certain such embodiments, the dose is the same and the dose frequency is varied to achieve the desired effect within five to thirteen weeks. In certain such embodiments, the dose increases over time and the dose frequency remains constant. In certain such embodiments, doses and dose frequency are selected to achieve a desired effect within six to 13 weeks. In certain such embodiments, doses and frequency are selected to achieve a desired effect within six weeks. In certain such embodiments, doses and frequency are selected to achieve a desired effect within seven weeks. In certain such embodiments, doses and frequency are selected to achieve a desired effect within eight weeks. In certain such embodiments, doses and frequency are selected to achieve a desired effect within nine weeks. In certain such embodiments, doses and frequency are selected to achieve a desired effect within ten weeks. In certain such embodiments, doses and frequency are selected to achieve a desired effect within eleven weeks. In certain such embodiments, doses and frequency are selected to achieve a desired effect within twelve weeks. In certain such embodiments, doses and frequency are selected to achieve a desired effect within thirteen weeks. In certain such embodiments, one or more doses of the induction phase is greater than one or more doses of the maintenance phase. In certain such embodiments, each of the induction doses is greater than each of the maintenance doses.

In certain embodiments, doses, dose frequency, and duration of the induction phase may be selected to achieve a desired effect within 13 to 25 weeks. In certain such embodiments, the dose is the same and the dose frequency is varied to achieve the desired effect within 13 to 25 weeks. In certain such embodiments, the dose increases over time and the dose frequency remains constant. In certain such embodiments, doses and frequency are selected to achieve a desired effect within thirteen weeks. In certain such embodiments, doses and frequency are selected to achieve a desired effect within fourteen weeks. In certain such embodiments, doses and frequency are selected to achieve a desired effect within fifteen weeks. In certain such embodiments, doses and frequency are selected to achieve a desired effect within sixteen weeks. In certain such embodiments, doses and frequency are selected to achieve a desired effect within seventeen weeks. In certain such embodiments, doses and frequency are selected to achieve a desired effect within eighteen weeks. In certain such embodiments, doses and frequency are selected to achieve a desired effect within nineteen weeks. In certain such embodiments, doses and frequency are selected to achieve a desired effect within twenty weeks. In certain such embodiments, doses and frequency are selected to achieve a desired effect within twenty-one weeks. In certain such embodiments, doses and frequency are selected to achieve a desired effect within twenty-two weeks. In certain such embodiments, doses and frequency are selected to achieve a desired effect within twenty-three weeks. In certain such embodiments, doses and frequency are selected to achieve a desired effect within twenty-four weeks. In certain such embodiments, doses and frequency are selected to achieve a desired effect within twenty-five weeks. In certain embodiments, one or more doses of the induction phase is less than one or more doses of the maintenance phase. In certain such embodiments, each dose of the induction phase is less than each dose of the maintenance phase.

In certain embodiments, it is desirable to achieve a desired effect as quickly as possible. In such embodiments, an induction phase with a high dose and/or high dose frequency may be desirable. Such embodiments may include administration to subjects with very high cholesterol concentrations.

In certain embodiments, it is desirable to mitigate an undesired side effect. In certain such embodiments, an induction phase with a low dose and/or low dose frequency and/or long duration may be desirable. For example, a long induction phase, with relatively low doses, may result in better tolerance of the pharmaceutical agent. Certain such embodiments, result in physiological changes that result in reduced overall side effects. In certain embodiments, such a dose regimen results in reduced liver toxicity when compared to higher initial doses and/or frequency. Such embodiments may include gradual increases of dose over time.

In certain embodiments in which a pharmaceutical composition is administered locally, the dosage regimen is selected to achieve a desired local concentration of a pharmaceutical agent of the present invention.

In certain embodiments, doses, dose frequency, and duration of the induction phase may be selected to achieve an acceptable safety profile. For example, in certain embodiments, such variables may be selected to mitigate toxicity of the pharmaceutical composition. In certain such embodiments, such variables are selected to mitigate liver toxicity. In certain such embodiments, such variables are selected to mitigate renal toxicity. In certain such embodiments, doses increase over time. In certain embodiments, one or more doses of the induction phase is lower than one or more doses of the maintenance phase. In certain such embodiments, a safety profile is not acceptable when ALT is 5-10 times the upper limit of normal. In certain such embodiments, a safety profile is not acceptable when ALT is 5-10 times the upper limit of normal, and bilirubin is elevated two or more times the upper limit of normal. In certain such embodiments, an acceptable safety profile comprises ALT elevations that are above three times the upper limit of normal, but do not exceed five times the upper limit of normal. In certain such embodiments, and acceptable safety profile comprises ALT elevations that are above three times the upper limit of normal, but do not exceed five times the upper limit of normal, and bilirubin elevations that do not exceed two times the upper limit of normal. In certain such embodiments, when administration of a pharmaceutical composition of the invention results in ALT elevations that are above three times the upper limit of normal, the dose and/or dose frequency is adjusted to mitigate the ALT elevation. In certain such embodiments, when administration of a pharmaceutical composition of the invention results in ALT elevations that are above three times the upper limit of normal, and bilirubin concentrations that are above two times the upper limit of normal, the dose and/or dose frequency is adjusted to mitigate the ALT elevation and bilirubin elevation. In certain such embodiments, the dose and/or dose frequency is adjusted to mitigate the bilirubin elevation alone.

In certain embodiments, the maintenance phase includes one, two three, four, five, six, seven, eight, nine, ten, eleven, twelve, thirteen, fourteen, fifteen, sixteen, seventeen, eighteen, nineteen, twenty, or more than twenty doses.

In certain embodiments, the maintenance phase lasts from one day to the lifetime of the subject. In certain embodiments the maintenance phase lasts from one week to twenty years as measured from administration of the last dose of the induction phase to administration of the last dose of the maintenance phase. In certain embodiments the maintenance phase lasts from two weeks to fifteen years as measured from administration of the last dose of the induction phase to administration of the last dose of the maintenance phase. In certain embodiments the maintenance phase lasts three weeks to ten years as measured from administration of the last dose of the induction phase to administration of the last dose of the maintenance phase. In certain embodiments the maintenance phase lasts from four weeks to ten years as measured from administration of the last dose of the induction phase to administration of the last dose of the maintenance phase. In certain embodiments the maintenance phase lasts as long as the dose continues to be needed, effective, and tolerated.

In certain embodiments where the maintenance phase includes more than one dose, the doses administered during the maintenance phase are all the same as one another. In certain embodiments, the doses administered during the maintenance phase are not all the same. In certain such embodiments, the doses increase over time. In certain embodiments, the doses decrease over time.

In certain embodiments, a maintenance dose is administered by parenteral administration. In certain such embodiments, the parenteral administration is subcutaneous administration. In certain such embodiments, the parenteral administration is intravenous infusion.

In certain embodiments, the doses during the maintenance phase are selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, the doses during the maintenance phase are selected from 25 mg, 50 mg, 75 mg, 100 mg, 150 mg, 200 mg, 250 mg, 300 mg, 350 mg, 400 mg, 500 mg, 600 mg, 700 mg, and 800 mg. In certain such embodiments, the doses during the maintenance phase are selected from 100 mg, 125 mg, 150 mg, 175 mg, 200 mg, 225 mg, 250 mg, 275 mg, 300 mg, 325 mg, 350 mg, 375 mg, and 400 mg. In certain such embodiments, the doses during the maintenance phase are selected from 100 mg, 125 mg, 150 mg, 175 mg, 200 mg, 225 mg, and 250 mg. In certain embodiments, the dose administered during the maintenance phase is 100 mg. In certain embodiments, the dose administered during the maintenance phase is 125 mg. In certain embodiments the dose administered during the maintenance phase is 150 mg. In certain embodiments the dose administered during the maintenance phase is 175 mg. In certain embodiments the dose administered during the maintenance phase is 200 mg. In certain embodiments the dose administered during the maintenance phase is 225 mg. In certain embodiments the dose administered during the maintenance phase is 250 mg. In certain embodiments the dose administered during the maintenance phase is 275 mg. In certain embodiments the dose administered during the maintenance phase is 300 mg.

In certain embodiments, where subcutaneous administration is desired, a maintenance dose may be administered in two or more subcutaneous injections. In certain such embodiments, when the desired maintenance dose requires a volume not easily accommodated by a single injection, two or more subcutaneous injections may be used to achieve the desired maintenance dose. In certain such embodiments, two or more subcutaneous injections may be used to administer the desired maintenance dose and minimize or eliminate an injection site reaction in a subject.

In certain embodiments, doses, dose frequency, and duration of the maintenance phase may be selected to achieve a desired effect. In certain embodiments, those variables are adjusted to result in a desired concentration of pharmaceutical agent in a subject. For example, in certain embodiments, dose and dose frequency are adjusted to provide plasma concentration of a pharmaceutical agent of the present invention at an amount sufficient to achieve a desired effect. In certain of such embodiments the plasma concentration is maintained above the minimal effective concentration (MEC). In certain embodiments, pharmaceutical compositions of the present invention are administered with a dosage regimen designed to maintain a concentration above the MEC for 10-90% of the time, between 30-90% of the time, or between 50-90% of the time.

In certain embodiments, doses, dose frequency, and duration of the maintenance phase may be selected to achieve a desired plasma trough concentration of a pharmaceutical composition. In certain such embodiments, the pharmaceutical composition is an oligonucleotide. In certain such embodiments, the desired plasma trough concentration is from 5-100 ng/mL. In certain such embodiments, the desired plasma trough concentration is from 5-50 ng/mL. In certain such embodiments, the desired plasma trough concentration is from 10-40 ng/mL. In certain such embodiments, the desired plasma trough concentration is from 15-35 ng/mL. In certain such embodiments, the desired plasma trough concentration is from 20-30 ng/mL.

In certain embodiments, doses, dose frequency, and duration of the maintenance phase may be selected to achieve a desired safety profile. For example, in certain embodiments, such variables may be selected to mitigate toxicity of the pharmaceutical composition. In certain such embodiments, such variables are selected to mitigate liver toxicity. In certain such embodiments, such variables are selected to mitigate renal toxicity. In certain such embodiments, doses increase over time.

In certain embodiments, doses, dose frequency, and duration of the maintenance phase may be adjusted from time to time to achieve a desired effect. In certain embodiments, subjects are monitored for effects (therapeutic and/or toxic effects) and doses, dose frequency, and/or duration of the maintenance phase may be adjusted based on the results of such monitoring.

It will be recognized by one of ordinary skill in the art that doses, dose frequency, and duration of the induction phase and for the maintenance phase may be manipulated independently to achieve a desired effect. For example, in certain embodiments, the invention provides dosage regimens listed in Tables 1-6, below. One of skill in the art will recognize that the variables in the table can be selected and combined independently. The table is included solely to illustrate how the variables may be combined and is does not limit the invention. Moreover, the present invention is not limited to the variables listed on the table.

In certain embodiments, a method of administering a pharmaceutical composition to a subject comprises an induction phase, wherein an induction dose of 200-400 mg is administered once per week for at least 8 weeks, followed by a maintenance phase, wherein a maintenance dose of 100-300 mg is administered at intervals ranging from one per week to once per three months, for as long as needed to sustain the desired effect. In certain embodiments the induction dose is administered once per week for 8-20 weeks. In certain embodiments the induction dose is administered once per week for 10-15 weeks. In certain embodiments, the induction dose is administered once per week for at least 12 weeks. In certain embodiments the induction dose is administered once per week for at least 14 weeks. In certain embodiments the induction dose is administered once per week for at least 16 weeks. In certain such embodiments, the induction dose is 200 mg. In certain such embodiments, the induction dose is 300 mg. In certain such embodiments, the induction dose is 400 mg. In certain such embodiments, the maintenance dose ranges from 200-300 mg. In certain such embodiments, the maintenance dose is 150 mg. In certain such embodiments, the maintenance dose is 200 mg. In certain such embodiments, the maintenance dose is 250 mg. In certain such embodiments, the maintenance dose is 300 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect. In certain such embodiments, the frequency of administration of the maintenance dose is adjusted to achieved desired efficacy and/or desired safety profile. In certain such embodiments, the frequency of the maintenance dose is adjusted to achieve a desired plasma trough concentration of oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the subject has homozygous familial hypercholesterolemia. In certain such embodiments, the subject has heterozygous familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 1.

In certain embodiments, a method of administering a pharmaceutical composition to a subject comprises an induction phase, wherein a 200 mg dose is administered once per week for 13 weeks, followed by a maintenance phase, wherein a dose ranging from 80-200 mg is administered at intervals ranging from once per week to once per three months, for as long as needed to sustain the desired effect. In certain such embodiments, the maintenance dose ranges from 100-150 mg. In certain such embodiments, the maintenance dose is 100 mg. In certain such embodiments, the maintenance dose is 125 mg. In certain such embodiments, the maintenance dose is 140 mg. In certain such embodiments, the maintenance dose is 150 mg. In certain such embodiments, the maintenance dose is 175 mg. In certain such embodiments, the maintenance dose is 180 mg. In certain such embodiments, the maintenance dose is 200 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect.

TABLE 1

Certain Dosing Regimens

| Induction Phase | | | Maintenance Phase | | |
|---|---|---|---|---|---|
| Doses | Dose frequency | Duration | Doses | Dose Frequency | Duration |
| 300 mg | Once/week | 8-20 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 8-20 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 8-20 weeks | 250 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 12-16 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 12-16 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 12-16 weeks | 250 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

In certain such embodiments, the frequency of administration of the maintenance dose is adjusted to achieved desired efficacy and/or desired safety profile. In certain such embodiments, the frequency of the maintenance dose is adjusted to achieve a desired plasma trough concentration of oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 2.

TABLE 2

Certain Dosing Regimens

| Induction Phase | | | Maintenance Phase | | |
|---|---|---|---|---|---|
| Doses | Dose frequency | Duration | Doses | Dose Frequency | Duration |
| 200 mg | Once/week | 13 weeks | 80 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 100 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 125 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 140 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 175 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 180 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 200 mg | Once/week | 13 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

In certain embodiments, a method of administering a pharmaceutical composition to a subject comprises an induction phase, wherein a 300 mg dose is administered once per week for 13 weeks, followed by a maintenance phase, wherein a dose ranging from 100-250 mg is administered at intervals ranging from once per week to once per three months, for as long as needed to sustain the desired effect. In certain such embodiments, the maintenance dose is 100 mg. In certain such embodiments, the maintenance dose is 125 mg. In certain such embodiments, the maintenance dose is 150 mg. In certain such embodiments, the maintenance dose is 175 mg. In certain such embodiments, the maintenance dose is 200 mg. In certain such embodiments, the maintenance dose is 250 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect. In certain such embodiments, the frequency of administration of the maintenance dose is adjusted to achieved desired efficacy and/or desired safety profile. In certain such embodiments, the frequency of the maintenance dose is adjusted to achieve a desired plasma trough concentration of oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, plasma trough concentration of the administered antisense oligonucleotide is 15-40 ng/mL. In certain such embodiments, the plasma trough concentration of the administered antisense oligonucleotide is 20-30 ng/mL. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 3.

TABLE 3

Certain Dosing Regimens

| Induction Phase | | | Maintenance Phase | | |
|---|---|---|---|---|---|
| Doses | Dose frequency | Duration | Doses | Dose Frequency | Duration |
| 300 mg | Once/week | 13 weeks | 100 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 13 weeks | 125 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 13 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 13 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 300 mg | Once/week | 13 weeks | 250 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

In certain embodiments, a method of administering a pharmaceutical composition to a subject comprises an induction phase, wherein a 100 mg dose is administered once per week for 13 weeks, followed by a maintenance phase, wherein a dose ranging from 100-300 mg is administered at intervals ranging from once per week to once per three months, for as long as needed to sustain the desired effect. In certain such embodiments, the dose ranges from 150-250 mg. In certain such embodiments, the maintenance dose is 100 mg. In certain such embodiments, the maintenance dose is 125 mg. In certain such embodiments, the maintenance dose is 150 mg. In certain such embodiments, the maintenance dose is 175 mg. In certain such embodiments, the maintenance dose is 200 mg. In certain such embodiments, the maintenance dose is 225 mg. In certain such embodiments, the maintenance dose is 250 mg. In certain such embodiments, the maintenance dose is 275 mg. In certain such embodiments, the maintenance dose is 300 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect. In certain such embodiments, the frequency of administration of the maintenance dose is adjusted to achieved desired efficacy and/or desired safety profile. In certain such embodiments, the frequency of the maintenance dose is adjusted to achieve a desired plasma trough concentration of oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 4.

TABLE 4

Certain Dosing Regimens

| Induction Phase | | | Maintenance Phase | | |
|---|---|---|---|---|---|
| Doses | Dose frequency | Duration | Doses | Dose Frequency | Duration |
| 100 mg | Once/week | 13 weeks | 100 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 125 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 175 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 225 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 250 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 275 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 13 weeks | 300 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

In certain embodiments, a method of administering a pharmaceutical composition to a subject comprises an induction phase, wherein a dose ranging from 100-200 mg is administered once per week for 13 weeks, followed by a maintenance phase, wherein a dose ranging from 100-300 mg is administered at intervals ranging from once per week to once per three months, for as long as needed to sustain the desired effect. In certain such embodiments, the induction dose is 100 mg. In certain such embodiments, the induction dose is 125 mg. In certain such embodiments, the induction dose is 150 mg. In certain such embodiments, the induction dose is 175 mg. In certain such embodiments, the induction dose is 200 mg. In certain such embodiments, an during an induction phase four doses of 100 mg are followed by five doses of 150 mg which are followed by four doses of 200 mg. In certain such embodiments during an induction phase four doses of 100 mg are followed by four doses of 150 mg which are followed by five doses of 200 mg. In certain such embodiments five doses of 100 mg are followed by four doses of 150 mg which are followed by four doses of 200 mg. In certain such embodiments, the maintenance dose is higher than the induction dose. In certain such embodiments, the maintenance dose is 100 mg. In certain such embodiments, the maintenance dose is 125 mg. In certain such embodiments, the maintenance dose is 150 mg. In certain such embodiments, the maintenance dose is 175 mg. In certain such embodiments, the maintenance dose is 200 mg. In certain such embodiments, the maintenance dose is 225 mg. In certain such embodiments, the maintenance dose is 250 mg. In certain such embodiments, the maintenance dose is 275 mg. In certain such embodiments, the maintenance dose is 300 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect. In certain such embodiments, the amount or frequency of the induction dose is adjusted to achieve desired efficacy and/or desired safety profile. In certain such embodiments, the amount or frequency of the induction dose is adjusted to achieve a desired plasma trough concentration of antisense oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, the amount or frequency of administration of the maintenance dose is adjusted to achieved desired efficacy and/or desired safety profile. In certain such embodiments, the frequency of the maintenance dose is adjusted to achieve a desired plasma trough concentration of oligonucleotide. In certain such embodiments, the plasma trough concentration of the administered antisense oligonucleotide is 15-40 ng/mL. In certain such embodiments, the plasma trough concentration of the administered antisense oligonucleotide is 20-30 ng/mL. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 5.

TABLE 5

Certain Dosing Regimens

| Induction Phase | | | Maintenance Phase | | |
|---|---|---|---|---|---|
| Doses | Dose frequency | Duration | Doses | Dose Frequency | Duration |
| 100 mg | Once/week, 4-5 weeks | 13 weeks total | 150 mg | Once/week | At least 6 months |
| 150 mg | Once/week, 4-5 weeks | | | Once/two weeks | At least one year |
| 200 mg | Once/week, 4-5 weeks | | | Once/three weeks | At least two years |
| | | | | Once/month | At least five years |
| | | | | Once/two months | Up to five years |
| | | | | Once/three months | Up to ten years |
| 100 mg | Once/week, 4-5 weeks | 13 weeks total | 175 mg | Once/week | At least 6 months |
| 150 mg | Once/week, 4-5 weeks | | | Once/two weeks | At least one year |
| 200 mg | Once/week, 4-5 weeks | | | Once/three weeks | At least two years |
| | | | | Once/month | At least five years |
| | | | | Once/two months | Up to five years |
| | | | | Once/three months | Up to ten years |
| 100 mg | Once/week, 4-5 weeks | 13 weeks total | 200 mg | Once/week | At least 6 months |
| 150 mg | Once/week, 4-5 weeks | | | Once/two weeks | At least one year |
| 200 mg | Once/week, 4-5 weeks | | | Once/three weeks | At least two years |
| | | | | Once/month | At least five years |
| | | | | Once/two months | Up to five years |
| | | | | Once/three months | Up to ten years |
| 100 mg | Once/week, 4-5 weeks | 13 weeks total | 225 mg | Once/week | At least 6 months |
| 150 mg | Once/week, 4-5 weeks | | | Once/two weeks | At least one year |
| 200 mg | Once/week, 4-5 weeks | | | Once/three weeks | At least two years |
| | | | | Once/month | At least five years |
| | | | | Once/two months | Up to five years |
| | | | | Once/three months | Up to ten years |

In certain embodiments, a method of administering a pharmaceutical composition to a subject comprises an induction phase, wherein a dose of 100 mg is administered once per week for 14-20 weeks, followed by a maintenance phase, wherein a dose ranging from 100-300 mg is administered at a frequency ranging from once per week to once per three months, for as long as needed to sustain the desired effect. In certain such embodiments, the induction phase is 16-20 weeks. In certain such embodiments, the duration of the induction phase is 14 weeks. In certain such embodiments, the duration of the induction phase is 15 weeks. In certain such embodiments, the duration of the induction phase is 16 weeks. In certain such embodiments, the duration of the induction phase is 17 weeks. In certain such embodiments, the duration of the induction phase is 18 weeks. In certain such embodiments, the duration of the induction phase is 19 weeks. In certain such embodiments, the duration of the induction phase is 20 weeks. In certain such embodiments, the maintenance dose is higher than the induction dose. In certain such embodiments, the maintenance dose ranges from 100-300 mg. In certain such embodiments, the maintenance dose ranges from 100-200 mg. In certain such embodiments, the maintenance dose is 100 mg. In certain such embodiments, the maintenance dose is 125 mg. In certain such embodiments, the maintenance dose is 150 mg. In certain such embodiments, the maintenance dose is 175 mg. In certain such embodiments, the maintenance dose is 200 mg. In certain such embodiments, the maintenance dose is 225 mg. In certain such embodiments, the maintenance dose is 250 mg. In certain such embodiments, the maintenance dose is 275 mg. In certain such embodiments, the maintenance dose is 300 mg. In certain such embodiments, the maintenance dose is administered once per week. In certain such embodiments, the maintenance dose is administered once per month. In certain such embodiments, the maintenance dose is administered once per three months. In certain such embodiments, the maintenance dose is administered for at least 6 months. In certain such embodiments, the maintenance dose is administered for at least one year. In certain such embodiments, the maintenance dose is administered for up to five years. In certain such embodiments the maintenance dose is administered for up to ten years. In certain such embodiments the maintenance dose is administered for as long as is necessary to sustain the desired effect. In certain such embodiments, the frequency of administration of the maintenance dose is adjusted to achieved desired efficacy and/or desired safety profile. In certain such embodiments, the desired effect is selected from reduced ApoB, reduced LDL-C, reduced VLDL-C, reduced IDL-C, reduced non-HDL-C, reduced serum triglycerides, reduced liver triglycerides, reduced Lp(a), reduced Ox-LDL-C, and reduced small dense LDL particles. In certain such embodiments, the subject has polygenic hypercholesterolemia. In certain such embodiments, the subject has familial hypercholesterolemia. In certain such embodiments, the pharmaceutical composition is co-administered with a statin. In certain such embodiments, the subject is intolerant to statins. In certain such embodiments, the subject is not meeting LDL-C target on current therapy. Non-limiting examples of certain dosing regimens are illustrated in Table 6.

TABLE 6

Certain Dosing Regimens

| Induction Phase | | | Maintenance Phase | | |
|---|---|---|---|---|---|
| Doses | Dose frequency | Duration | Doses | Dose Frequency | Duration |
| 100 mg | Once/week | 14-20 weeks | 100 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 125 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 150 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 175 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 200 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 225 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

TABLE 6-continued

Certain Dosing Regimens

| Induction Phase | | | Maintenance Phase | | |
|---|---|---|---|---|---|
| Doses | Dose frequency | Duration | Doses | Dose Frequency | Duration |
| 100 mg | Once/week | 14-20 weeks | 275 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |
| 100 mg | Once/week | 14-20 weeks | 300 mg | Once/week | At least 6 months |
| | | | | Once/two weeks | At least one year |
| | | | | Once/three weeks | At least two years |
| | | | | Once/month | At least five years |
| | | | | Once/two months | Up to five years |
| | | | | Once/three months | Up to ten years |

In a particular embodiment, a method of administering a pharmaceutical composition to a subject comprises an induction phase, wherein a dose ranging from 100-300 mg is administered once per week for 13 weeks, followed by a maintenance phase, wherein a dose ranging from 80-200 mg is administered once per week for as long as needed, effective, and/or tolerated. In certain of such embodiments, the pharmaceutical composition is administered subcutaneously during the induction phase and/or the maintenance phase. In certain of such embodiments, the subject is afflicted with familial hypercholesterolemia (either heterozygous or homozygous), non-familial hypercholesterolemia, or polygenic hypercholesterolemia. In certain of such embodiments, the maintenance phase lasts from one day to the end of the subject's lifetime or any fraction thereof as discussed above. In certain of such embodiments, the induction dose is 100 mg, and the maintenance dose is 80 mg, 100 mg, 140 mg, 180 mg, or 200 mg. In certain of such embodiments, the induction dose is 200 mg, and the maintenance dose is 80 mg, 100 mg, 140 mg, 180 mg, or 200 mg. In certain of such embodiments, the induction dose is 300 mg, and the maintenance dose is 80 mg, 100 mg, 140 mg, 180 mg, or 200 mg.

In certain of such embodiments, the administration at the end of the induction phase achieves a reduction in plasma concentration of ApoB of from about −28% to −65%. In certain of such embodiments, the administration after 13 weeks of the maintenance phase achieves a reduction in plasma concentration of ApoB of from about −32% to −48%, from about −35% to about −52%, from about −40% to about −60%, from about −43% to about −65%, or from about −45% to about −67%. In certain of such embodiments, the administration at the end of the induction phase achieves a reduction in plasma concentration of LDL-Col from about −26% to −60%. In certain of such embodiments, the administration after 13 weeks of the maintenance phase achieves a reduction in plasma concentration of LDL-Col from about −29% to −44%, from about −32% to about −48%, from about −37% to about −55%, from about −40% to about −61%, or from about −42% to about −63%.

In certain of such embodiments, the administration at the end of the induction phase achieves a plasma trough concentration of an oligonucleotide administered as part of the pharmaceutical composition of from about 11 to 38 ng/mL. In certain of such embodiments, the administration after 13 weeks of the maintenance phase achieves a plasma trough concentration of an oligonucleotide administered as part of the pharmaceutical composition of from about 7 to 27 ng/mL, from about 8 to 31 ng/mL, from about 11 to 38 ng/mL, from about 13 to 46 ng/mL, or from about 14 to 50 ng/mL. In certain of such embodiments, the administration at the end of the induction phase achieves a liver concentration of an oligonucleotide administered as part of the pharmaceutical composition of from about 55 to 190 µg/G. In certain of such embodiments, the administration after 13 weeks of the maintenance phase achieves a liver concentration of an oligonucleotide administered as part of the pharmaceutical composition of from about 38 to 133 µg/G, from about 44 to 152 µg/G, from about 55 to 190 µg/G, from about 66 to 228 µg/G, or from about 7 to 247 µg/G.

In certain of such embodiments, the administration at the end of the induction phase achieves a reduction in plasma concentration of ApoB of from about −34% to −77%. In certain of such embodiments, the administration after 13 weeks of the maintenance phase achieves a reduction in plasma concentration of ApoB of from about −38% to −58%, from about −43% to about −65%, from about −47% to about −70%, or from about −49% to about −74%. In certain of such embodiments, the administration at the end of the induction phase achieves a reduction in plasma concentration of LDL-Col from about −31% to −73%. In certain of such embodiments, the administration after 13 weeks of the maintenance phase achieves a reduction in plasma concentration of LDL-Col from about −35% to −54%, from about −40% to about −61%, from about −44% to about −66%, or from about −46% to about −70%.

In certain of such embodiments, the administration at the end of the induction phase achieves a plasma trough concentration of an oligonucleotide administered as part of the pharmaceutical composition of from about 16 to 57 ng/mL. In certain of such embodiments, the administration after 13 weeks of the maintenance phase achieves a plasma trough concentration of an oligonucleotide administered as part of the pharmaceutical composition of from about 10 to 37 ng/mL, from about 13 to 46 ng/mL, from about 16 to 55 ng/mL, or from about 18 to 65 ng/mL. In certain of such embodiments, the administration at the end of the induction phase achieves a liver concentration of an oligonucleotide administered as part of the pharmaceutical composition of from about 82 to 285 µg/G. In certain of such embodiments, the administration after 13 weeks of the maintenance phase achieves a liver concentration of an oligonucleotide administered as part of the pharmaceutical composition of from about 52 to 181 µg/G, from about 66 to 228 µg/G, from about 80 to 276 µg/G, or from about 94 to 323 µg/G.

In another particular embodiment, a method of administering a pharmaceutical composition to a subject comprises an induction phase, wherein a dose ranging from 100-300 mg is administered once per week for 13 weeks, followed by a maintenance phase, wherein a dose ranging from 100-200 mg is administered once per week for as long as needed, effective, and/or tolerated, wherein the efficacy and/or the tolerability of the antisense oligonucleotide is monitored during the induction phase, the maintenance phase, or both, or any portion thereof. In certain of such embodiments, the pharmaceutical composition is administered subcutaneously during the induction phase and/or the maintenance phase. In certain of such embodiments, the subject is afflicted with familial hypercholesterolemia (either heterozygous or homozygous), non-familial hypercholesterolemia, or polygenic hypercholesterolemia. In certain of such embodiments, the maintenance phase lasts from one day to the end of the subject's lifetime or any fraction thereof as discussed above.

In certain of such embodiments, the rate of reduction in the plasma concentration of ApoB is monitored during the induction and/or maintenance phases. In certain of such embodiments, the plasma concentration of ApoB is monitored during the induction and/or maintenance phases. In certain embodiments, if the rate of reduction in the plasma concentration of ApoB exceeds 30 mg/dL*day, the dose of pharmaceutical composition is altered, e.g., reduced. In certain embodiments, if the rate of reduction in the plasma concentration of ApoB exceeds 30 mg/dL*day, the frequency of administration of pharmaceutical composition is altered, e.g., reduced. In certain embodiments, if the plasma concentration of ApoB falls below about 50 mg/dL, the dose of pharmaceutical composition is altered, e.g., reduced. In certain embodiments, if the plasma concentration of ApoB falls below about 50 mg/dL, the frequency of administration of pharmaceutical composition is altered, e.g., reduced. In certain embodiments, if the plasma concentration of ApoB falls below about 60 mg/dL, the dose of pharmaceutical composition is altered, e.g., reduced. In certain embodiments, if the plasma concentration of ApoB falls below about 60 mg/dL, the frequency of administration of pharmaceutical composition is altered, e.g., reduced.

In certain embodiments, if the rate of reduction in the plasma concentration of ApoB exceeds 30 mg/dL*day and the plasma concentration of ApoB falls below about 50 mg/dL, the dose of pharmaceutical composition is altered, e.g., reduced. In certain embodiments, if the rate of reduction in the plasma concentration of ApoB exceeds 30 mg/dL*day and the plasma concentration of ApoB falls below about 50 mg/dL, the frequency of administration of pharmaceutical composition is altered, e.g., reduced. In certain embodiments, if the rate of reduction in the plasma concentration of ApoB exceeds 30 mg/dL*day and the plasma concentration of ApoB falls below about 60 mg/dL, the dose of pharmaceutical composition is altered, e.g., reduced. In certain embodiments, if the rate of reduction in the plasma concentration of ApoB exceeds 30 mg/dL*day and the plasma concentration of ApoB falls below about 60 mg/dL, the frequency of administration of pharmaceutical composition is altered, e.g., reduced.

In another particular embodiment, a method of administering a pharmaceutical composition to a subject comprises an induction phase, wherein a dose ranging from 100 to 200 mg is administered once per week for 13 weeks, and a maintenance phase, wherein a dose ranging from 200 to 300 mg is administered once per week for as long as needed, effective, and/or tolerated, wherein the tolerability and/or efficacy of the pharmaceutical composition is assessed during or at the end of the induction phase, or any portion thereof. In certain of such embodiments, the dose of the maintenance phase is increased relative to the dose of the maintenance phase if the dose of the induction phase is well-tolerated and treatment goals are not met. In certain of such embodiments, the pharmaceutical composition is administered subcutaneously during the induction phase and/or the maintenance phase. In certain of such embodiments, the subject is afflicted with familial hypercholesterolemia (either heterozygous or homozygous), non-familial hypercholesterolemia, or polygenic hypercholesterolemia. In certain of such embodiments, the maintenance phase lasts from one day to the end of the subject's lifetime or any fraction thereof as discussed above. In certain of such embodiments, the induction dose is 100 mg, and the maintenance dose is 200 mg. In certain of such embodiments, the induction dose is 200 mg, and the maintenance dose is 300 mg. In certain embodiments, the treatment goals are assessed by monitoring plasma concentration of ApoB, LDL-C, VLDL-C, non-HDL-C, HDL-C, ApoA1, total cholesterol, triglycerides, and Lp(a). In certain embodiments, tolerability is assessed by monitoring ALT activity, AST activity, and plasma bilirubin concentrations.

In certain of such embodiments, the administration at the end of the induction phase achieves a reduction in plasma concentration of ApoB of from about −17% to −40%. In certain of such embodiments, the administration after 26 weeks of the maintenance phase achieves a reduction in plasma concentration of ApoB of from about −42% to −63%. In certain of such embodiments, the administration at the end of the induction phase achieves a reduction in plasma concentration of LDL-Col from about −14% to −35%. In certain of such embodiments, the administration after 13 weeks of the maintenance phase achieves a reduction in plasma concentration of LDL-Col from about −39% to −60%.

In certain of such embodiments, the administration at the end of the induction phase achieves a plasma trough concentration of an oligonucleotide administered as part of the pharmaceutical composition of from about 5 to 19 ng/mL. In certain of such embodiments, the administration after 26 weeks of the maintenance phase achieves a plasma trough concentration of an oligonucleotide administered as part of the pharmaceutical composition of from about 12 to 44 ng/mL. In certain of such embodiments, the administration at the end of the induction phase achieves a liver concentration of an oligonucleotide administered as part of the pharmaceutical composition of from about 27 to 95 µg/G. In certain of such embodiments, the administration after 26 weeks of the maintenance phase achieves a liver concentration of an oligonucleotide administered as part of the pharmaceutical composition of from about 63 to 220 µg/G.

In another particular embodiment, a method of administering a pharmaceutical composition to a subject comprises an induction phase, wherein a dose ranging from 100 to 200 mg is administered once per week for 13 weeks, and a maintenance phase, wherein a dose ranging from 200 to 300 mg is administered once every one or two weeks for as long as needed, effective, and/or tolerated, wherein the tolerability and/or efficacy of the pharmaceutical composition is assessed during or at the end of the induction phase, or any portion thereof. In certain of such embodiments, the frequency of administration of dose during the maintenance phase is reduced relative if the dose of the induction phase is not well-tolerated and/or treatment goals are met. In certain of such embodiments, the pharmaceutical composition is administered subcutaneously during the induction phase and/or the maintenance phase. In certain of such embodiments, the subject is afflicted with familial hypercholesterolemia (either heterozygous or homozygous), non-familial hypercholesterolemia, or polygenic hypercholesterolemia. In certain of such embodiments, the maintenance phase lasts from one day to the end of the subject's lifetime or any fraction thereof as discussed above. In certain of such embodiments, the induction dose is 100 mg, and the maintenance dose is 200 mg. In certain of such embodiments, the induction dose is 200 mg, and the maintenance dose is 300 mg. In certain embodiments, the treatment goals are assessed by monitoring plasma concentration of ApoB, LDL-C, VLDL-C, non-HDL-C, HDL-C, ApoA1, total cholesterol, triglycerides, and Lp(a). In certain embodiments, tolerability is assessed by monitoring ALT levels, AST levels, plasma bilirubin concentrations or total bilirubin.

D. CERTAIN COMBINATION THERAPIES

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include lipid-lowering agents. In certain such embodiments, pharmaceutical agents that may be co-administered with a pharmaceutical composition of the present invention include, but are not limited to atorvastatin, simvastatin, rosuvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor.

In certain embodiments, a co-administered lipid-lowering agent is an oligonucleotide selected from an oligonucleotide targeted to PCSK9, an oligonucleotide targeted to ACAT-2, an oligonucleotide targeted to endothelial lipase, and an oligonucleotide targeted to CETP.

In certain embodiments, a co-administered pharmaceutical agent is a bile acid sequestrant. In certain such embodiments, the bile acid sequestrant is selected from cholestyramine, colestipol, and colesevelam.

In certain embodiments, a co-administered pharmaceutical agent is a nicotinic acid. In certain such embodiments, the nicotinic acid is selected from immediate release nicotinic acid, extended release nicotinic acid, and sustained release nicotinic acid.

In certain embodiments, a co-administered pharmaceutical agent is a fibric acid. In certain such embodiments, a fibric acid is selected from gemfibrozil, fenofibrate, clofibrate, bezafibrate, and ciprofibrate.

Further examples of pharmaceutical agents that may be co-administered with a pharmaceutical composition of the present invention include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjuction with a lipid-lowering therapy. In certain such embodiments, a lipid-lowering therapy is therapeutic lifestyle change. In certain such embodiments, a lipid-lowering therapy is LDL apheresis.

E. CERTAIN INDICATIONS

In certain embodiments, the invention provides methods of treating a subject comprising administering one or more pharmaceutical agents of the present invention. In certain embodiments, such subject has hypercholesterolemia, hyperlipidemia, non-familial hypercholesterolemia, familial hypercholesterolemia, heterozygous familial hypercholesterolemia, homozygous familial hypercholesterolemia, coronary heart disease, atherosclerosis, mixed dyslipidemia, diabetic dyslipidemia. In certain embodiments, such subject has been identified as having one or more CHD risk equivalents. In certain embodiments, such subject has been identified has having major risk factors for coronary heart disease. In certain embodiments, such subject has been identified as having one or more CHD risk factors. In certain embodiments, such subject has been identified being at risk for atherosclerosis. In certain embodiments, such subject has been identified as having a history of coronary heart disease. In certain embodiments, such subject has been identified as having a family history of early onset coronary heart disease.

In certain embodiments, the subject has been identified as having elevated cholesterol. In certain embodiments, the subject has been identified as in need of lipid lowering therapy. In certain such embodiments, the subject has been identified as in need of lipid-lowering therapy according to the guidelines established by the Adult Treatment Panel III of the National Cholesterol Education Program (NCEP) in 2001 and modified by the Coordinating Committee of the NCEP in 2004 (Grundy et al., *Circulation*, 2004, 110, 227-239). In certain such embodiments, the subject in need of lipid-lowering therapy has LDL-C above 190 mg/dL. In certain such embodiments, the subject in need of lipid-lowering therapy has LDL-C above 160 mg/dL. In certain such embodiments the subject in need of lipid-lowering therapy has LDL-C above 130 mg/dL. In certain such embodiments, the subject in need of lipid-lowering therapy should maintain LDL-C below 160 mg/dL. In certain such embodiments, the subject in need of lipid-lowering therapy should maintain LDL-C below 130 mg/dL. In certain such embodiments, the subject in need of lipid-lowering therapy should maintain LDL-C below 100 mg/dL. In certain such embodiments the subject should maintain LDL-C below 70 mg/dL.

In certain embodiments, the invention provides methods for reducing ApoB concentration in a subject. In certain embodiments, the invention provides method for reducing ApoB-containing lipoprotein concentration in a subject. In certain embodiments, the invention provides methods for reducing LDL-C concentration in a subject. In certain embodiments, the invention provides methods for reducing VLDL-C concentration in a subject. In certain embodiments, the invention provides methods for reducing IDL-C concentration in a subject. In certain embodiments, the invention provides methods for reducing non-HDL-C concentration in a subject. In certain embodiments, the invention provides methods for reducing Lp(a) concentration in a subject. In certain embodiments, the invention provides methods for reducing serum triglyceride concentration in a subject. In certain embodiments the invention provides methods for reducing Ox-LDL-C concentration in a subject. In certain such embodiments, the reduction in ApoB, LDL-C, VLDL-C, IDL-C, total cholesterol, non-HDL-C, Lp(a), triglycerides, or Ox-LDL-C is, independently, selected from at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, and at least 100%. In certain such embodiments, the reduction in ApoB, LDL-C, VLDL-C, IDL-C, total cholesterol, non-HDL-C, Lp(a), triglycerides, or Ox-LDL-C is, independently, selected from at least 20%, at least 30%, at least 40%, at least 50%, at least 60%, and at least 70%. In certain such embodiments, the reduction in ApoB, LDL-C, VLDL-C, IDL-C, total cholesterol, non-HDL-C, Lp(a), triglycerides, or Ox-LDL-C is, independently, selected from at least 40%, at least 50%, at least 60%, and at least 70%.

In certain embodiments, the invention provides method for raising HDL-C concentration in a subject.

In certain embodiments, the methods provided by the present invention do not lower HDL-C. In certain embodiments, the methods provided by the present invention do not result in accumulation of lipids in the liver.

In certain embodiments, the invention provides methods for lowering ApoB concentration in a subject while reducing side effects associated with treatment. In certain such embodiments, a side effect is liver toxicity. In certain such embodiments, a side effect is abnormal liver function. In certain such embodiments, a side effect is liver inflammation or other adverse event that occurs in the liver. In certain such embodiments, a side effect is elevated alanine aminotransferase (ALT). In certain such embodiments, a side effect is elevated aspartate aminotransferase (AST). For example, certain dosing regimens of the present invention result in effective lowering of ApoB concentration with less liver toxicity than has been observed from studies employing different dosing regimens. In certain embodiments, dosing regimens of the present invention result in effective lowering of ApoB with less elevation in ALT. In certain such embodiments, the amount of an induction dose administered is lower than the amount of a maintenance dose administered.

In certain embodiments, the invention provides methods for lowering ApoB concentration in a subject who is not reaching target LDL-C levels as a result of lipid-lowering therapy. In certain such embodiments, ISIS 301012 is the only lipid-lowering agent administered to the subject. In certain such embodiments, the subject has not complied with recommended lipid-lowering therapy. In certain such embodiments, a pharmaceutical composition of the invention is co-administered with an additional different lipid-lowering therapy. In certain such embodiments, an additional lipid-lowering therapy is LDL-apheresis. In certain such embodiments, an additional lipid-lowering therapy is a statin. In certain such embodiments, an additional lipid-lowering therapy is ezetimibe.

In certain embodiments, the invention provides methods for lowering ApoB concentration in a statin-intolerant subject. In certain such embodiments, the subject has creatine kinase concentration increases as a result of statin administration. In certain such embodiments, the subject has liver function abnormalities as a result of statin administration. In certain such embodiments the subject has muscle aches as a result of statin administration. In certain such embodiments the subject has central nervous system side effects as a result of statin administration. In certain embodiments, the subject has not complied with recommended statin administration.

In certain embodiments, the invention provides methods for lowering liver triglycerides in a subject. In certain such embodiments, the subject has elevated liver triglycerides. In certain such embodiments, the subject has steatohepatitis. In certain such embodiments, the subject has steatosis. In certain such embodiments, liver triglyceride levels are measured by magnetic resonance imaging.

In certain embodiments, the invention provides methods for reducing coronary heart disease risk in a subject. In certain embodiments the invention provides methods for slowing the progression of atherosclerosis in a subject. In certain such embodiments the invention provides methods for stopping the progression of atherosclerosis in a subject. In certain such embodiments the invention provides methods for reducing the size and/or prevalence of atherosclerotic plaques in a subject. In certain embodiments the methods provided reduce a subject's risk of developing atherosclerosis.

In certain embodiments the methods provided improve the cardiovascular outcome in a subject. In certain such embodiments improved cardiovascular outcome is the reduction of the risk of developing coronary heart disease. In certain such embodiments, improved cardiovascular outcome is a reduction in the occurance of one or more major cardiovascular events, which include, but are not limited to, death, myocardial infarction, reinfarction, stroke, cardiogenic shock, pulmonary edema, cardiac arrest, and atrial dysrhythmia. In certain such embodiments, the improved cardiovascular outcome is evidenced by improved carotid intimal media thickness. In certain such embodiments, improved carotid intimal media thickness is a decrease in thickness. In certain such embodiments, improved carotid intimal media thickness is a prevention an increase of intimal media thickness.

NONLIMITING DISCLOSURE AND INCORPORATION BY REFERENCE

While the present invention has been described with specificity in accordance with certain embodiments, the following examples serve only to illustrate the invention and are not intended to limit the same. Each of the references, GenBank accession numbers, and the like recited in the present application is incorporated herein by reference in its entirety.

EXAMPLES

Example 1

Subjects

Three subjects were identified as having homozygous familial hypercholesterolemia using the following criteria: (1) documented history of LDL-C above 500 mg/dL in the absence of lipid-lowering therapy; and (2) at least one of (a) genetic testing confirming 2 mutated LDL-receptor genes; (b) tendinous and/or cutaneous xanthoma prior to age 10 years; or (c) documentation of elevated LDL-C prior to lipid-lowering therapy consistent with heterozygous familial hypercholesterolemia in both parents (if a parent's medical history was not available, a history of coronary heart disease in a first degree male relative younger than 55 years old or first degree female relative younger than 60 years old was used as a criterion in place of a parent's medical history).
Dose Regimen The three subjects received a 300 mg dose of ISIS 301012 on Days 1, 4, 8, 11, 15, 22, 29, 36, 43, 50, 57, 64, 71, 78, and 85, as summarized in the table, below. ISIS 301012 was administered subcutaneously. The four doses on Days 1, 4, 8, and 11 were administered to achieve estimated ISIS 301012 levels in liver tissue that are approximately 60-90% of steady-state concentration. The subjects were monitored for concentrations of ApoB, LDL-C, VLDL-C, non-HDL-C, HDL-C, ApoA1, total cholesterol, triglycerides, and Lp(a). Subjects were also monitored to ensure acceptable safety profiles. The subjects also received one or more lipid-lowering therapies.

TABLE 7

Co-administration of ISIS 301012 with one or more additional lipid-lowering therapies in subjects with homozygous familial hypercholesterolemia.

| Induction Phase | | | Maintenance Phase | | |
| --- | --- | --- | --- | --- | --- |
| Doses | Dose frequency | Duration | Doses | Dose Frequency | Duration |
| 300 mg | Twice/week | 2 weeks | 300 mg | Once/week | 11 weeks |

Results

At Day 43, after 9 doses of 301012, both ApoB and LDL-C were reduced by approximately 30% (n=3) compared to the subject's concentration at baseline, prior to ISIS 301012 administration.

At Day 78, after 14 doses of ISIS 301012, (n=2; one subject had not yet received reached the $14^{th}$ dose at time of this writing) both ApoB and LDL-C were reduced by approximately 50%. VLDL-C concentration was reduced by approximately 30%. Non-HDL-C concentration reductions ranged from 32 to 50%. Total cholesterol concentration reductions ranged from 30% to 46%. Triglyceride concentration reductions ranged from 29% to 33%. Lp(a) concentration reductions of 19%, 20%, and 54% were observed. HDL-C concentration increases of 5%, 7%, and 40% were observed.

These data demonstrate that ISIS 301012 lowered lipid concentrations in subjects having familial hypercholesterolemia. LDL-C reductions in subjects having familial hypercholesterolemia were observed later during the administration period relative to LDL-C reductions in subjects having non-familial hypercholesterolemia, suggesting that a longer induction period in familial hypercholesterolemic subjects may provide a therapeutic benefit such subjects. For example, an induction period of at least 8 weeks may provide a therapeutic benefit to subjects having familial hypercholesterolemia, whereas shorter induction periods or induction periods with lower doses may be sufficient for subjects with non-familial hypercholesterolemia Example 2

Rate and Magnitude of ApoB Reduction with ISIS 301012

Without being bound to a particular theory, it is believed that mild increases in ALT levels seen during initial treatment with ISIS 301012 in dose regimens having a high multi-dose loading period, reflect extreme lipid lowering activity. Particularly, the rise in ALT can be attributed to the rate and magnitude of lipid lowering. An ALT rise can be lessened or prevented by a dosing regimen that limits the rate and magnitude of ApoB reduction during the induction or initial dosing period, approximately the first 15 to 90 days of treatment. Thus, for the first time, the rate and magnitude of ApoB reduction has been correlated with ALT levels.
Subjects Hypercholesterolemics on stable statin therapy. ApoB levels and ALT levels were determined for the subjects in the trial. Table 8 provides the ApoB levels for individual subjects and resulting ALT levels.

TABLE 8

ApoB and ALT Levels for Individual Subjects

| Dose | Subject | Rate of ApoB Reduction (mg/dL/day) | Min ApoB Concentration (mg/dL) | Max ALT (U/L) |
| --- | --- | --- | --- | --- |
| 400 mg on day 1, 8, 10, 12, 15, 22 and 29 | 5043 | 2.5 | 44 | 130 |
| 400 mg on day 1, 8, 10, 12, 15, 22 and 29 | 5044 | 1.7 | 60 | 175 |
| 400 mg on day 1, 8, 10, 12, 15, 22 and 29 | 5124 | 2.5 | 30 | 125 |

TABLE 8-continued

ApoB and ALT Levels for Individual Subjects

| Dose | Subject | Rate of ApoB Reduction (mg/dL/day) | Min ApoB Concentration (mg/dL) | Max ALT (U/L) |
|---|---|---|---|---|
| 300 mg on day 1, 8, 10, 12, 15, 22 and 29 | 4097 | 3.5 | 55 | 190 |
| 300 mg on day 1, 8, 10, 12, 15, 22 and 29 | 4011 | 2.8 | 45 | 100 |
| 300 mg on day 1, 8, 10, 12, 15, 22 and 29 | 4035 | 3.5 | 25 | 270 |
| 200 mg on day 1, 8, 10, 12, 15, 22 and 29 | 3083 | 2.3 | 60 | 140 |
| 200 mg on day 1, 8, 10, 12, 15, 22 and 29 | 3097 | 1.8 | 60 | 120 |
| 200 mg on day 1, 8, 10, 12, 15, 22 and 29 | 3174 | 1.8 | 50 | 125 |
| 30 mg on day 1, 8, 10, 12, 15, 22 and 29 | 1035 | 0.5 | 70 | 25 |

Results

The data provided indicate that increases in ALT levels can occur when subjects fall below two thresholds, a minimum ApoB concentration of about 60 mg/dL or less during the first 15 to 60 days and an average rate of reduction of 1.5 mg/dL/day or greater within the first 15 to 60 days of treatment can result in an elevated ALT of about 100 U/L or greater. This may also be considered in terms of approximately a 15% drop per day or greater or a change of more than 30 mg/dL over the first 30 days. An ALT of 100 U/L is considered greater than three times the upper limit of normal. The upper limit of normal for ALT concentration is approximately 30 U/L. A value three times above such limit would be considered unfavorable.

Two hundred and forty four subjects from 6 different clinical trials including healthy volunteers, familial hypercholesterolemic subject, polygenic hypercholesterolemic subject and subject on statin therapy have been evaluated and threshold levels of ApoB have been associated with ALT levels. Table 8 shows the number of subjects having a positive slope (rate of reduction of ApoB greater than 1 mg/dL/day) and who violated the threshold for magnitude of reduction (ApoB concentration of less than 60 mg/dL). 80% of such subjects (32 of 41) experienced and ALT rise of 3XULN or above.

TABLE 9

Slope and Threshold Analysis

|  | Positive Slope | Negative Slope |
|---|---|---|
| Threshold Violated | 41 (32) | 5 (0) |
| Threshold Intact | 24 (6) | 156 (8) |

N = 244
18(0) - uninterpretable due to borderline threshold levels

Example 3

Reduction in ApoB with ISIS 301012 in Subjects with Polygenic Hypersholeterolemia Subjects Subjects were identified as having polygenic hypercholesterolemia. Subjects typically had LDL-C levels greater than about 130 mg/dL in the absence of lipid-lowering therapy.

Dosing

Three groups of 8 patients each were dosed. The groups were dosed with 200, 300 or 400 mg of ISIS 301012 once per week for 13 weeks with no initial loading. ISIS 301012 was administered by subcutaneous injection.

TABLE 10

ApoB levels and and ALT Elevations

|  | 200 mg/wk (mg/dL) | 300 mg/wk (mg/dL) | 400 mg/wk (mg/dL) |
|---|---|---|---|
| ApoB Baseline | 130 (93-150) | 139 (109-160) | 150 (118-172 |
| ApoB at 2 wks (% change from baseline) | −47 | −61 | >−70** |
| ALT Elevations* | 0 | 0 | 5 |

*ALT elevations ≥3XULN on two consecutive measurements at least 7 days apart
**4 of 8 patients reached the lower limit of detection for ApoB Results The drop in ApoB from baseline at 2 weeks for the 200 and 300 mg/kg dose groups resulted, on average in a rate and/or magnitude drop that did not meet or exceed the threshold requirements identified in example 2. There were no ALT elevations in the three treatment groups during the dosing period. The drop in ApoB from baseline at 2 weeks for the 400 mg/kg dose group resulted on average in a rate and/or magnitude drop that did exceed the threshold requirements identified in example 2 and resulted in ALT increases 3XULN.

Example 4

Predictive Effect of Long Induction at High Dose

Subjects

Subjects are identified as having familial or polygenic hypercholesterolemia. Subjects typically have LDL-C levels greater than about 120 mg/dL in the absence of lipid-lowering therapy.

Dose Regimen

Subjects are initially dosed using a long induction at higher dose then the maintenance dose. Group A receives a 200 mg dose of ISIS 301012 once a week for 13 weeks. Group B receives a 300 mg dose of ISIS 301012 once a week for 13 weeks. After 13 weeks, subjects are placed on a reduced maintenance dose regimen. Group A receives a 100 mg dose of ISIS 301012 once weekly and Group B receives a 200 mg dose of ISIS 301012 once weekly. ISIS 301012 can be administered subcutaneously or by any other method provided herein. The 13 week induction doses are administered to achieve estimated ISIS 301012 levels in liver tissue that are approximately 60-90% of steady-state concentration. The subjects are monitored for concentrations of ApoB, LDL-C, VLDL-C, non-HDL-C, HDL-C, ApoA1, total cholesterol, triglycerides, and Lp(a). Subjects are also monitored to ensure acceptable safety profiles including ALT, AST and bilirubin.

TABLE 11

Administration of ISIS 301012

| | Induction Phase | | Maintenance Phase | |
|---|---|---|---|---|
| Group | Dose/ Dose frequency | Duration | Dose/ Dose frequence | Duration |
| A | 200 mg/wk | 13 wks | 100 mg/wk | 52 |
| B | 300 mg/wk | 13 wks | 200 mg/wk | 52 |

Although 100 and 200 mg/wk are exemplified above, maintenance doses can be higher or lower. Table 9, 10, 11 and 12 provide predicted values based on modeled dosing regimens. The models are based on the clinical trial data obtained to date and particularly the polygenic monotherapy trials in Example 3. Based on an induction of either 200 or 300 mg/wk, ApoB and LDL levels as well as plasma trough and liver concentrations are predicted for the induction and maintenance phases,

TABLE 12

Predicted Effect (% change from baseline) at end of 13-week 200 mg/wk induction and 13-week maintenance

| Cohort | Week | ApoB Mean | (95% C.I.) | LDL Mean | (95% C.I.) |
|---|---|---|---|---|---|
| | | Induction: | | | |
| 200 mg/wk | 14 | −46.9 | (−65.3 to −28.5) | −43.3 | (−60.3 to −26.3) |
| | | Maintenance: | | | |
| 80 mg/wk | 28 | −40.0 | (−47.9 to −32.2) | −36.3 | (−43.4 to −29.2) |
| 100 mg/wk | 28 | −43.7 | (−52.2 to −35.1) | −40.0 | (−47.8 to −32.2) |
| 140 mg/wk | 28 | −49.6 | (−59.3 to −39.9) | −46.0 | (−55.1 to −37.0) |
| 180 mg/wk | 28 | −54.2 | (−64.8 to −43.5) | −50.7 | (−60.6 to −40.7) |
| 200 mg/wk | 28 | −56.0 | (−67.0 to −45.0) | −52.6 | (−62.9 to −42.3) |

TABLE 13

Predicted PK at end of 13-week 200 mg/wk induction and 13-week maintenance

| Cohort | Day | Predicted Plasma Ctrough a (ng/mL) Mean | (95% C.I.) | Predicted Liver Conc. (µg/g) Mean | (95% C.I.) |
|---|---|---|---|---|---|
| | | Induction: | | | |
| 200 mg/wk | 92 | 24.5 | (11.1 to 38.0) | 123 | (55.3 to 190) |
| | | Maintenance: | | | |
| 80 mg/wk | 183 | 17.2 | (7.8 to 26.6) | 86.0 | (38.8 to 133) |
| 100 mg/wk | 183 | 19.7 | (8.9 to 30.4) | 98.3 | (44.3 to 152) |
| 140 mg/wk | 183 | 24.6 | (11.1 to 38.0) | 123 | (55.4 to 190) |
| 180 mg/wk | 183 | 29.5 | (13.3 to 45.6) | 147 | (66.5 to 228) |
| 200 mg/wk | 183 | 31.9 | (14.4 to 49.40 | 159 | (72.0 to 247) |

Group A Results

At the end of the 13 week induction phase, the mean liver concentration of 301012 in Group A is predicted to be approximately 123 ug/g. This concentration is maintained at a maintenance dose of about 100 mg/wk. At the end of the 13 week induction, the mean percent change in ApoB levels from baseline is approximately 46.9%. At week 13 of maintenance, the mean percent change in ApoB levels from baseline is maintained. At the end of the 13 week induction, the mean percent change in LDL levels from baseline is approximately 43.3%. At week 13 of maintenance, the mean percent change in LDL levels from baseline is maintained. At the end of the 13 week induction phase, plasma trough concentration is approximately 24.5 ng/mL. At week 13 of maintenance, the plasma trough concentration is maintained.

TABLE 14

Predicted Effect (% change from baseline) at end of 13-week 300 mg induction and 13-week maintenance

| Cohort | Week | ApoB Mean (95% C.I.) | LDL Mean (95% C.I.) |
|---|---|---|---|
| | | Induction: | |
| 300 mg/wk | 14 | −56.0 (−77.9 to −34.0) | −52.5 (−73.1 to −31.9) |
| | | Maintenance: | |
| 100 mg/wk | 28 | −48.3 (−57.8 to 38.8) | −44.7 (−53.5 to −35.9) |
| 150 mg/wk | 28 | −54.2 (−64.8 to −43.6) | −50.7 (−60.6 to −40.7) |
| 200 mg/wk | 28 | −58.4 (−69.9 to −47.0) | −55.0 (−65.8 to −44.2) |
| 250 mg/wk | 28 | −61.6 (−73.7 to −49.5) | −58.3 (−69.7 to −46.8) |

TABLE 15

Predicted PK at end of 13-week 300 mg induction (based on polygenic monotherapy trials in Example 3) and 13-week maintenance

| Cohort | Day | Predicted Plasma Ctrough a (ng/mL) Mean | (95% C.I.) | Predicted Liver Conc. (µg/g) Mean | (95% C.I.) |
|---|---|---|---|---|---|
| | | Induction: | | | |
| 300 mg/wk | 92 | 36.8 | (16.6 to 56.9) | 184 | (82.9 to 285) |
| | | Maintenance: | | | |
| 100 mg/wk | 183 | 23.4 | (10.5 to 36.2) | 117 | (52.7 to 181) |
| 150 mg/wk | 183 | 29.5 | (13.3 to 45.7) | 147 | (66.5 to 228) |
| 200 mg/wk | 183 | 35.6 | (16.1 to 55.1) | 178 | (80.3 to 276) |
| 250 mg/wk | 183 | 41.7 | (18.8 to 64.6) | 209 | (94.2 to 323) |

Group B Results

At the end of the 13 week induction phase, the mean liver concentration of 301012 in Group B is predicted to be approximately 184 ug/g. This concentration is maintained at a maintenance dose of about 200 mg/wk. At the end of the 13 week induction, the mean percent change in ApoB levels from baseline is approximately 56%. At week 13 of maintenance, the mean percent change in ApoB levels from baseline is maintained. At the end of the 13 week induction, the mean percent change in LDL levels from baseline is approximately 52.5%. At week 13 of maintenance, the mean percent change in LDL levels from baseline is maintained. At the end of the 13 week induction phase, plasma trough concentration is approximately 36.8 ng/mL. At week 13 of maintenance, the plasma trough concentration is maintained.

Example 5

Predictive Effect of Long Induction at Low Dose

Subjects

Subjects are identified as having polygenic or familial hypercholesterolemia. Subjects typically have LDL-C levels greater than about 130 mg/dL in the absence of lipid-lowering therapy.

Dose Regimen

Subjects are initially dosed using a long induction at lower dose then the maintenance dose. Group A receives a 100 mg dose of ISIS 301012 once a week for 13 weeks. Group B receives a 200 mg dose of ISIS 301012 once a week for 13 weeks. After 13 weeks, subjects are evaluated based on tolerability and effectiveness with respect to treatment goals. If dosing is well tolerated and treatment goals are not being met, patients are placed on an elevated maintenance dose regimen.

Group A receives a 200 mg dose of ISIS 301012 once weekly and Group B receives a 300 mg dose of ISIS 301012 once weekly. ISIS 301012 is administered subcutaneously. The 13 week induction doses are administered to achieve estimated ISIS 301012 levels in liver tissue that are approximately 60-90% of steady-state concentration. The subjects are monitored for concentrations of ApoB, LDL-C, VLDL-C, non-HDL-C, HDL-C, ApoA1, total cholesterol, triglycerides, and Lp(a). Subjects were also monitored to ensure acceptable safety profiles (including ALT, AST and bilirubin.

TABLE 16

Administration of ISIS 301012

| | Induction Phase | | Maintenance Phase | |
|---|---|---|---|---|
| Group | Dose/ Dose frequency | Duration | Dose/ Dose frequence | Duration |
| A | 100 mg/wk | 13 wks | 200 mg/wk | 52 |
| B | 200 mg/wk | 13 wks | 300 mg/wk | 52 |

Table 14 and 15 provide predicted values based on a modeled dosing regimen. The model is based on the clinical trial data obtained to date and particularly the polygenic monotherapy trials in Example 3. Based on an induction of either 100 mg/wk, ApoB and LDL levels as well as plasma trough and liver concentrations are predicted for the induction and maintenance phases,

TABLE 17

Predicted Effect (% change from baseline) for a 6-month trial with a 13 week priming regimen of 100 mg/wk and a 26 week maintenance of 200 mg/wk

| | | ApoB | LDL |
|---|---|---|---|
| Cohort | Week | Mean (95% C.I.) | Mean (95% C.I.) |
| | | End of 13 weeks: | |
| 100 mg/wk for 13 wks | 14 | −28.4 (−39.5 to −17.3) | −24.5 (−34.0 to −14.9) |
| | | End of 26 weeks: | |
| 200 mg/wk for 13 wks | 28 | −53.1 (−63.5 to −42.7) | −49.6 (−59.3 to −39.9) |

TABLE 18

Predicted PK for a 6-month trial with a 13 week priming regimen and a 26 week maintenance

| | | Predicted Plasma Ctrough a (ng/mL) | Predicted Liver Conc. (µg/g) |
|---|---|---|---|
| Cohort | Day | Mean (95% C.I.) | Mean (95% C.I.) |
| | | End of 13 weeks: | |
| 100 mg/wkl for 13 wks | 92 | 12.3 (5.5 to 19.0) | 61.3 (27.6 to 95) |
| | | End of 26 weeks: | |
| 200 mg/wk for 13 wks | 183 | 28.2 (12.7 to 43.7) | 141 (63.6 to 218) |

Group A Results

At the end of the 13 week induction phase, the mean liver concentration of 301012 in Group A is predicted to be approximately 61.3 ug/g. This concentration is increased to 141 after 13 weeks of the 200 mg/wk maintenance dose. At the end of the 13 week induction, the mean percent change in ApoB levels from baseline is approximately 28.4%. At week 26 of dosing, the mean percent change in ApoB levels from baseline is 53.1%. At the end of the 13 week induction, the mean percent change in LDL levels from baseline is approximately 24.5%. After 13 weeks of maintenance, the mean percent change in LDL levels from baseline is increased to 49.6%. At the end of the 13 week induction phase, plasma trough concentration is approximately 12.3 ng/mL. At week 13 of maintenance, the plasma trough concentration is predicted to increased to 28.2 ng/mL.

Example 6

Once Every Other Week Interval Dosing

Subjects

Subjects were identified as having polygenic hypercholesterolemia. Subjects typically had LDL-C levels greater than about 120 mg/dl in the absence of lipid-lowering therapy.

Dose Regimen

ISIS 301012 was administered by s.c. injection at 200 mg twice weekly for two weeks followed by a dose of 200 mg every other week for 11 weeks.

TABLE 19

ApoB levels at Two and Fourteen Weeks of Treatment

| | 200 mg every other week(mg/dL) |
|---|---|
| ApoB Baseline | 129 (100-185) |
| ApoB at 2 wks** | −23 |
| ApoB at 14 wks** | −28.4 |
| ALT Elevations* | 0 |

*ALT elevations ≥3XULN
**(% change from baseline)

Results

The results show the effectiveness of delivering ISIS 301012 in a once every other week regimen with no associated ALT elevations.

Example 7

Predicted Effect of Once Every Other Week Interval Dosing With Induction Phase

Subjects

Subjects are identified as having familial hypercholesterolemia and represent a lower tolerance population such as diabetics and mix-hyperlipidemics. Subjects typically have LDL-C levels greater than about 130 mg/dL in the absence of lipid-lowering therapy.

Dose Regimen

ISIS 301012 is administered by s.c. injection at a dose of 200 mg every week for 13 weeks and then 200 mg every other week for 52 weeks.

TABLE 20

Predicted Effect (% change from baseline) for a 6-month trial with a 13 week induction of 200 mg/wk and a predicted 13 week maintenance of 200 mg every other week

| | | ApoB | LDL |
|---|---|---|---|
| Cohort | Week | Mean (95% C.I.) | Mean (95% C.I.) |
| | | End of 13 weeks: | |
| 200 mg/wk for 13 wks | 14 | −46.9 (−65.3 to −28.5) | −43.3 (−60.3 to −26.3) |

TABLE 20-continued

Predicted Effect (% change from baseline) for a 6-month trial with a 13 week induction of 200 mg/wk and a predicted 13 week maintenance of 200 mg every other week

| Cohort | Week | ApoB Mean (95% C.I.) | LDL Mean (95% C.I.) |
|---|---|---|---|
| | | End of 26 weeks: | |
| 200 mg every other wk for 13 wks | 26 | −43.7 (−52.2 to −35.1) | −40.0 (−47.8 to −32.2) |

TABLE 21

Predicted PK for a 6-month trial with a 13 week induction of 200 mg/wk and a predicted 13 week maintenance of 200 mg every other week

| Cohort | Week | Predicted Plasma Ctrough a (ng/mL) Mean (95% C.I.) | Predicted Liver Conc. (μg/g) Mean (95% C.I.) |
|---|---|---|---|
| | | End of 13 weeks: | |
| 200 mg/wk for 13 wks | 14 | 24.5 (11.1 to 38.0) | 123 (55.3 to 190) |
| | | End of 26 weeks: | |
| 200 mg every other wk for 13 wks | 26 | 19.7 (8.9 to 30.4) | 98.3 (44.3 to 152) |

Results

The results show the delivering ISIS 301012 in a once every other week regimen can be and effective regimen and is not likely to result in elevated ALT levels.

Example 8

Predicted Effect of Once Monthly Interval Dosing With Induction Phase

Subjects

Subjects are identified as having familial hypercholesterolemia and represent a lower tolerance population such as diabetics and mix-hyperlipidemics. Subjects typically have LDL-C levels greater than about 130 mg/dL in the absence of lipid-lowering therapy.

Dose Regimen

ISIS 301012 is administered by s.c. injection or by any method provided herein. In certain embodiments, subjects can be dosed at 200, 400 or 800 mg every month for 12 months (FIG. 1). In other embodiments, subjects are dosed at 200 mg/wk for 1 month and then 200, 400 or 600 mg once monthly for 11 months (FIG. 2). In other embodiments, subjects are dosed at 200 mg/wk for 3 month and then 200, 400 or 600 mg once monthly for 9 months (FIG. 3).

Results

The results predict that delivering ISIS 301012 in a once monthly regimen with or without an induction period can be an effective regimen and is not likely to result in elevated ALT levels.

What is claimed is:

1. A method comprising administering to a subject a pharmaceutical composition comprising an antisense oligonucleotide complementary to a nucleic acid encoding human apolipoprotein B-100, wherein the administering comprises an induction phase, wherein a 210 mg dose of the antisense oligonucleotide per week is administered in two or more administrations for at least 13 weeks, followed by a maintenance phase, wherein a 210 mg dose of the antisense oligonucleotide per week is administered in two or more administrations.

2. The method of claim 1, wherein tolerability or effectiveness of the antisense oligonucleotide are assessed during or at the end of the induction phase, or a portion thereof.

3. The method of claim 1, wherein said administration comprises subcutaneous administration.

4. The method of claim 1, wherein effectiveness of the antisense oligonucleotide is assessed by monitoring ApoB, LDL-C, VLDL-C, IDL-C, non-HDL-C, serum triglycerides, liver triglycerides, Lp(a), Ox-LDL-C, or small dense LDL particle concentration in the plasma of said subject.

5. The method of claim 1, wherein said subject has hypercholesterolemia.

6. The method of claim 5, wherein said subject has polygenic hypercholesterolemia.

7. The method of claim 5, wherein said subject has familial hypercholesterolemia.

8. The method of claim 7, wherein said subject has homozygous familial hypercholesterolemia.

9. The method of claim 7, wherein said subject has heterozygous familial hypercholesterolemia.

10. The method of claim 1, wherein said subject has mixed dyslipidemia.

11. The method of claim 1, wherein said subject has been treated by a statin.

12. The method of claim 11, wherein said subject failed to meet LDL-cholesterol target on statin therapy.

13. The method of claim 1, wherein said administering of said pharmaceutical composition results in ApoB reduction of at least 10%.

14. The method of claim 13 wherein said ApoB reduction is between 10% and 80%, between 20% and 70%, between 30% and 60%, or between 30% and 70%.

15. The method of claim 1, wherein said administering of said pharmaceutical composition results in a LDL-cholesterol reduction of at least 10%.

16. The method of claim 15, wherein said LDL-cholesterol reduction is at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

17. The method of claim 1, wherein said administering of said pharmaceutical composition results in Lp(a) reduction of at least 10%.

18. The method of claim 1, wherein said administering of said pharmaceutical composition results in a small LDL-particle reduction of at least 10%.

19. The method of claim 1, wherein said administering of said pharmaceutical composition results in a non-HDL-cholesterol reduction of at least 10%.

20. The method of claim 1, wherein said administering of said pharmaceutical composition results in reduced coronary heart disease risk in the subject.

21. The method of claim 1, wherein said administering of said pharmaceutical composition slows or stops the progression of atherosclerosis in the subject.

22. The method of claim 1, wherein said administering of said pharmaceutical composition results in improved cardiovascular outcome the subject.

23. The method of claim 22, wherein said improved cardiovascular outcome is increased HDL-cholesterol.

24. The method of claim 22, wherein said administering results in reductions in LDL-cholesterol, triglycerides, or small LDL particles, or a combination thereof.

25. The method of claim 1, wherein the antisense oligonucleotide is at least 90% complementary to a nucleic acid encoding human ApoB.

26. The method of claim 1, wherein the antisense oligonucleotide is ISIS 301012.

27. A method comprising administering to a subject a pharmaceutical composition comprising a 210 mg dose of an antisense oligonucleotide complementary to a nucleic acid encoding human apolipoprotein B-100 per week in two or more administrations, wherein the antisense oligonucleotide is ISIS 301012, wherein said administering of said pharmaceutical composition results in antisense oligonucleotide plasma trough levels between 5 and 100 ng/mL.

28. The method of claim 27, wherein said administering of said pharmaceutical composition results in antisense oligonucleotide plasma trough levels between 5 and 50 ng/mL.

29. The method of claim 27, wherein said administering of said pharmaceutical composition results in antisense oligonucleotide plasma trough levels between 10 and 40 ng/mL.

30. The method of claim 27, wherein said administering of said pharmaceutical composition results in antisense oligonucleotide plasma trough levels between 15 and 35 ng/mL.

31. The method of claim 27, wherein said administering of said pharmaceutical composition results in antisense oligonucleotide plasma trough levels between 20 and 30 ng/mL.

* * * * *

SEQUENCE LISTING

```
<160> NUMBER OF SEQ ID NOS: 2

<210> SEQ ID NO 1
<211> LENGTH: 14121
<212> TYPE: DNA
<213> ORGANISM: Homo sapiens

<400> SEQUENCE: 1
attcccaccg ggacctgcgg ggctgagtgc ccttctcggt tgctgccgct gaggagcccg      60
cccagccagc cagggccgcg aggccgaggc caggccgcag cccaggagcc gccccaccgc     120
agctggcgat ggacccgccg aggcccgcgc tgctggcgct gctggcgctg cctgcgctgc     180
tgctgctgct gctggcgggc gccagggccg aagaggaaat gctggaaaat gtcagcctgg     240
tctgtccaaa agatgcgacc cgattcaagc acctccggaa gtacacatac aactatgagg     300
ctgagagttc cagtggagtc cctgggactg ctgattcaag aagtgccacc aggatcaact     360
gcaaggttga gctggaggtt ccccagctct gcagcttcat cctgaagacc agccagtgca     420
ccctgaaaga ggtgtatggc ttcaaccctg agggcaaagc cttgctgaag aaaaccaaga     480
actctgagga gtttgctgca gccatgtcca ggtatgagct caagctggcc attccagaag     540
ggaagcaggt tttcctttac ccggagaaag atgaacctac ttacatcctg aacatcaaga     600
ggggcatcat ttctgccctc ctggttcccc cagagacaga agaagccaag caagtgttgt     660
ttctggatac cgtgtatgga aactgctcca ctcactttac cgtcaagacg aggaagggca     720
atgtggcaac agaaatatcc actgaaagag acctggggca gtgtgatcgc ttcaagccca     780
```

```
tccgcacagg catcagccca cttgctctca tcaaaggcat gacccgcccc ttgtcaactc     840
tgatcagcag cagccagtcc tgtcagtaca cactggacgc taagaggaag catgtggcag     900
aagccatctg caaggagcaa cacctcttcc tgcctttctc ctacaacaat aagtatggga     960
tggtagcaca agtgacacag actttgaaac ttgaagacac accaaagatc aacagccgct    1020
tctttggtga aggtactaag aagatgggcc tcgcatttga gagcaccaaa tccacatcac    1080
ctccaaagca ggccgaagct gttttgaaga ctctccagga actgaaaaaa ctaaccatct    1140
ctgagcaaaa tatccagaga gctaatctct tcaataagct ggttactgag ctgagaggcc    1200
tcagtgatga agcagtcaca tctctcttgc cacagctgat tgaggtgtcc agccccatca    1260
ctttacaagc cttggttcag tgtggacagc ctcagtgctc cactcacatc ctccagtggc    1320
tgaaacgtgt gcatgccaac ccccttctga tagatgtggt cacctacctg gtggccctga    1380
tccccgagcc ctcagcacag cagctgcgag agatcttcaa catggcgagg gatcagcgca    1440
gccgagccac cttgtatgcg ctgagccacg cggtcaacaa ctatcataag acaaacccta    1500
cagggaccca ggagctgctg gacattgcta attacctgat ggaacagatt caagatgact    1560
gcactgggga tgaagattac acctatttga ttctgcgggt cattggaaat atgggccaaa    1620
ccatggagca gttaactcca gaactcaagt cttcaatcct caaatgtgtc caagtacaa    1680
agccatcact gatgatccag aaagctgcca tccaggctct gcggaaaatg agcctaaag    1740
acaaggacca ggaggttctt cttcagactt tccttgatga tgcttctccg ggagataagc    1800
gactggctgc ctatcttatg ttgatgagga gtccttcaca ggcagatatt aacaaaattg    1860
tccaaattct accatgggaa cagaatgagc aagtgaagaa ctttgtggct tcccatattg    1920
ccaatatctt gaactcagaa gaattggata tccaagatct gaaaaagtta gtgaaagaag    1980
ctctgaaaga atctcaactt ccaactgtca tggacttcag aaaattctct cggaactatc    2040
aactctacaa atctgtttct cttccatcac ttgacccagc ctcagccaaa atagaaggga    2100
atcttatatt tgatccaaat aactaccttc ctaaagaaag catgctgaaa actaccctca    2160
ctgcctttgg atttgcttca gctgacctca tcgagattgg cttggaagga aaaggctttg    2220
agccaacatt ggaagctctt tttgggaagc aaggattttt cccagacagt gtcaacaaag    2280
ctttgtactg ggttaatggt caagttcctg atggtgtctc taaggtctta gtggaccact    2340
ttggctatac caaagatgat aaacatgagc aggatatggt aaatggaata atgctcagtg    2400
ttgagaagct gattaaagat ttgaaatcca agaagtcccc ggaagccaga gcctacctcc    2460
gcatcttggg agaggagctt ggttttgcca gtctccatga cctccagctc tgggaaaagc    2520
tgcttctgat gggtgcccgc actctgcagg ggatccccca tgattggaga ggtcatca    2580
ggaagggctc aaagaatgac ttttttcttc actacatctt catggagaat gcctttgaac    2640
tccccactgg agctggatta cagttgcaaa tatcttcatc tggagtcatt gctcccggag    2700
ccaaggctgg agtaaaactg gaagtagcca acatgcaggc tgaactggtg caaaaccct    2760
ccgtgtctgt ggagtttgtg acaaatatgg gcatcatcat tccggacttc gctaggagtg    2820
gggtccagat gaacaccaac ttcttccacg agtcgggtct ggaggctcat gttgccctaa    2880
aagctgggaa gctgaagttt atcattcctt ccccaaagag accagtcaag ctgctcagtg    2940
gaggcaacac attacatttg gtctctacca ccaaaacgga ggtgatccca cctctcattg    3000
agaacaggca gtcctggtca gtttgcaagc aagtctttcc tggcctgaat tactgcacct    3060
caggcgctta ctccaacgcc agctccacag actccgcctc ctactatccg ctgaccgggg    3120
acaccagatt agagctggaa ctgaggccta caggagagat tgagcagtat tctgtcagcg    3180
```

```
caacctatga gctccagaga gaggacagag ccttggtgga tacccctgaag tttgtaactc   3240 aagcagaagg tgcgaagcag actgaggcta ccatgacatt caaatataat cggcagagta   3300
tgaccttgtc cagtgaagtc caaattccgg attttgatgt tgacctcgga acaatcctca   3360
gagttaatga tgaatctact gagggcaaaa cgtcttacag actcaccctg gacattcaga   3420
acaagaaaat tactgaggtc gccctcatgg gccacctaag ttgtgacaca aaggaagaaa   3480
gaaaaatcaa gggtgttatt tccatacccc gtttgcaagc agaagccaga agtgagatcc   3540
tcgcccactg gtcgcctgcc aaactgcttc tccaaatgga ctcatctgct acagcttatg   3600
gctccacagt ttccaagagg gtggcatggc attatgatga agagaagatt gaatttgaat   3660
ggaacacagg caccaatgta gataccaaaa aaatgacttc caatttccct gtggatctct   3720
ccgattatcc taagagcttg catatgtatg ctaatagact cctggatcac agagtccctg   3780
aaacagacat gactttccgg cacgtgggtt ccaaattaat agttgcaatg agctcatggc   3840
ttcagaaggc atctgggagt cttccttata cccagacttt gcaagaccac ctcaatagcc   3900
tgaaggagtt caacctccag aacatgggat tgccagactt ccacatccca gaaaacctct   3960
tcttaaaaag cgatggccgg gtcaaatata ccttgaacaa gaacagtttg aaaattgaga   4020 ttccttttgcc ttttggtggc aaatcctcca gagatctaaa gatgttagag actgttagga   4080
caccagccct ccacttcaag tctgtgggat tccatctgcc atctcgagag ttccaagtcc   4140 ctactttttac cattcccaag ttgtatcaac tgcaagtgcc tctcctgggt gttctagacc   4200
tctccacgaa tgtctacagc aacttgtaca actggtccgc ctcctacagt ggtgggcaaca   4260 ccagcacaga ccatttcagc cttcgggctc gttaccacat gaaggctgac tctgtggttg   4320
acctgctttc ctacaatgtg caaggatctg gagaaacaac atatgaccac aagaatacgt   4380
tcacactatc atgtgatggg tctctacgcc acaaatttct agattcgaat atcaaattca   4440
gtcatgtaga aaaacttgga aacaacccag tctcaaaagg tttactaata ttcgatgcat   4500
ctagttcctg gggaccacag atgtctgctt cagttcattt ggactccaaa aagaaacagc   4560
atttgtttgt caaagaagtc aagattgatg ggcagttcag agtctcttcg ttctatgcta   4620
aaggcacata tggcctgtct tgtcagaggg atcctaacac tggccggctc aatggagagt   4680
ccaacctgag gtttaactcc tcctacctcc aaggcaccaa ccagataaca ggaagatatg   4740
aagatggaac cctctcccctc acctccacct ctgatctgca aagtggcatc attaaaaata   4800
ctgcttccct aaagtatgag aactacgagc tgactttaaa atctgacacc aatgggaagt   4860
ataagaactt tgccacttct aacaagatgg atatgacctt ctctaagcaa aatgcactgc   4920
tgcgttctga atatcaggct gattacgagt cattgaggtt cttcagcctg ctttctggat   4980
cactaaattc ccatggtctt gagttaaatg ctgacatctt aggcactgac aaaattaata   5040
gtggtgctca caaggcgaca ctaaggattg gccaagatgg aatatctacc agtgcaacga   5100
ccaacttgaa gtgtagtctc ctggtgctgg agaatgagct gaatgcagag cttggcctct   5160
ctggggcatc tatgaaatta acaacaaatg gccgcttcag ggaacacaat gcaaaattca   5220
gtctggatgg gaaagccgcc ctcacagagc tatcactggg aagtgcttat caggccatga   5280
ttctgggtgt cgacagcaaa aacatttca acttcaaggt cagtcaagaa ggacttaagc   5340
tctcaaatga catgatgggc tcatatgctg aaatgaaatt tgaccacaca aacagtctga   5400
acattgcagg cttatcactg gacttctctt caaaacttga caacatttac agctctgaca   5460
agttttataa gcaaactgtt aatttacagc tacagcccta ttctctggta actactttaa   5520
```

```
acagtgacct gaaatacaat gctctggatc tcaccaacaa tgggaaacta cggctagaac    5580
ccctgaagct gcatgtggct ggtaacctaa aaggagccta ccaaaataat gaaataaaac    5640
acatctatgc catctcttct gctgccttat cagcaagcta taaagcagac actgttgcta    5700
aggttcaggg tgtggagttt agccatcggc tcaacacaga catcgctggg ctggcttcag    5760
ccattgacat gagcacaaac tataattcag actcactgca tttcagcaat gtcttccgtt    5820
ctgtaatggc cccgtttacc atgaccatcg atgcacatac aaatggcaat gggaaactcg    5880
ctctctgggg agaacatact gggcagctgt atagcaaatt cctgttgaaa gcagaacctc    5940
tggcatttac tttctctcat gattacaaag gctccacaag tcatcatctc gtgtctagga    6000
aaagcatcag tgcagctctt gaacacaaag tcagtgccct gcttactcca gctgagcaga    6060
caggcacctg gaaactcaag acccaattta caacaatga atacagccag gacttggatg    6120
cttacaacac taaagataaa attggcgtgg agcttactgg acgaactctg gctgacctaa    6180
ctctactaga ctccccaatt aaagtgccac ttttactcag tgagcccatc aatatcattg    6240
atgctttaga gatgagagat gccgttgaga agccccaaga atttacaatt gttgcttttg    6300
taaagtatga taaaaaccaa gatgttcact ccattaacct cccatttttt gagaccttgc    6360
aagaatattt tgagaggaat cgacaaacca ttatagttgt agtggaaaac gtacagagaa    6420
acctgaagca catcaatatt gatcaatttg taagaaaata cagagcagcc ctgggaaaac    6480
tcccacagca agctaatgat tatctgaatt cattcaattg ggagagacaa gtttcacatg    6540
ccaaggagaa actgactgct ctcacaaaaa agtatagaat tacagaaaat gatatacaaa    6600
ttgcattaga tgatgccaaa atcaacttta atgaaaaact atctcaactg cagacatata    6660
tgatacaatt tgatcagtat attaaagata gttatgattt acatgatttg aaaatagcta    6720
ttgctaatat tattgatgaa atcattgaaa aattaaaaag tcttgatgag cactatcata    6780
tccgtgtaaa tttagtaaaa acaatccatg atctacattt gtttattgaa atattgatt    6840 ttaacaaaag tggaagtagt actgcatcct ggattcaaaa tgtggatact aagtaccaaa    6900
tcagaatcca gatacaagaa aaactgcagc agcttaagag acacatacag aatatagaca    6960
tccagcacct agctggaaag ttaaaacaac acattgaggc tattgatgtt agagtgcttt    7020
tagatcaatt gggaactaca atttcatttg aaagaataaa tgatgttctt gagcatgtca    7080
aacactttgt tataaatctt attggggatt ttgaagtagc tgagaaaatc aatgccttca    7140
gagccaaagt ccatgagtta atcgagaggt atgaagtaga ccaacaaatc caggttttaa    7200
tggataaatt agtagagttg acccaccaat acaagttgaa ggagactatt cagaagctaa    7260
gcaatgtcct acaacaagtt aagataaaag attactttga gaaattggtt ggatttattg    7320
atgatgctgt gaagaagctt aatgaattat cttttaaaac attcattgaa gatgttaaca    7380
aattccttga catgttgata aagaaattaa agtcatttga ttaccaccag tttgtagatg    7440
aaaccaatga caaaatccgt gaggtgactc agagactcaa tggtgaaatt caggctctgg    7500
aactaccaca aaaagctgaa gcattaaaac tgttttaga ggaaaccaag gccacagttg    7560
cagtgtatct ggaaagccta caggacacca aaataacctt aatcatcaat tggttacagg    7620
aggctttaag ttcagcatct ttggctcaca tgaaggccaa attccgagag actctagaag    7680
atacacgaga ccgaatgtat caaatggaca ttcagcagga acttcaacga tacctgtctc    7740
tggtaggcca ggtttatagc acacttgtca cctacatttc tgattggtgg actcttgctg    7800
ctaagaacct tactgacttt gcagagcaat attctatcca agattgggct aaacgtatga    7860
aagcattggt agagcaaggg ttcactgttc ctgaaatcaa gaccatcctt gggaccatgc    7920
```

```
ctgcctttga agtcagtctt caggctcttc agaaagctac cttccagaca cctgatttta   7980
tagtccccct aacagatttg aggattccat cagttcagat aaacttcaaa gacttaaaaa   8040
atataaaaat cccatccagg ttttccacac cagaatttac catccttaac accttccaca   8100
ttccttcctt tacaattgac tttgtcgaaa tgaaagtaaa gatcatcaga accattgacc   8160
agatgcagaa cagtgagctg cagtggcccg ttccagatat atatctcagg gatctgaagg   8220
tggaggacat tcctctagcg agaatcaccc tgccagactt ccgtttacca gaaatcgcaa   8280
ttccagaatt cataatccca actctcaacc ttaatgattt tcaagttcct gaccttcaca   8340
taccagaatt ccagcttccc cacatctcac acacaattga agtacctact tttggcaagc   8400
tatacagtat tctgaaaatc caatctcctc ttttcacatt agatgcaaat gctgacatag   8460
ggaatggaac cacctcagca aacgaagcag gtatcgcagc ttccatcact gccaaaggag   8520
agtccaaatt agaagttctc aattttgatt ttcaagcaaa tgcacaactc tcaaacccta   8580
agattaatcc gctggctctg aaggagtcag tgaagttctc cagcaagtac ctgagaacgg   8640
agcatgggag tgaaatgctg ttttttggaa atgctattga gggaaaatca aacacagtgg   8700
caagtttaca cacagaaaaa aatacactgg agcttagtaa tggagtgatt gtcaagataa   8760
acaatcagct taccctggat agcaacacta aatacttcca caaattgaac atccccaaac   8820
tggacttctc tagtcaggct gacctgcgca acgagatcaa gacactgttg aaagctggcc   8880
acatagcatg gacttcttct ggaaaagggt catggaaatg ggcctgcccc agattctcag   8940
atgagggaac acatgaatca caaattagtt tcaccataga aggacccctc acttcctttg   9000
gactgtccaa taagatcaat agcaaacacc taagagtaaa ccaaaacttg gtttatgaat   9060
ctggctccct caacttttct aaacttgaaa ttcaatcaca agtcgattcc cagcatgtgg   9120
gccacagtgt tctaactgct aaaggcatgg cactgtttgg agaagggaag gcagagttta   9180
ctgggaggca tgatgctcat ttaaatggaa aggttattgg aactttgaaa aattctcttt   9240
tcttttcagc ccagccattt gagatcacgg catccacaaa caatgaaggg aatttgaaag   9300
ttcgttttcc attaaggtta acagggaaga tagacttcct gaataactat gcactgtttc   9360
tgagtcccag tgcccagcaa gcaagttggc aagtaagtgc taggttcaat cagtataagt   9420
acaaccaaaa tttctctgct ggaaacaacg agaacattat ggaggcccat gtaggaataa   9480
atggagaagc aaatctggat ttcttaaaca ttcctttaac aattcctgaa atgcgtctac   9540
cttacacaat aatcacaact cctccactga agatttctc tctatgggaa aaaacaggct   9600
tgaaggaatt cttgaaaacg acaaagcaat catttgattt aagtgtaaaa gctcagtata   9660
agaaaaacaa acacaggcat tccatcacaa atcctttggc tgtgctttgt gagtttatca   9720
gtcagagcat caaatccttt gacaggcatt ttgaaaaaaa cagaaacaat gcattagatt   9780
ttgtcaccaa atcctataat gaaacaaaaa ttaagtttga taagtacaaa gctgaaaaat   9840
ctcacgacga gctccccagg acctttcaaa ttcctggata cactgttcca gttgtcaatg   9900
ttgaagtgtc tccattcacc atagagatgt cggcattcgg ctatgtgttc ccaaaagcag   9960
tcagcatgcc tagtttctcc atcctaggtt ctgacgtccg tgtgccttca tacacattaa  10020
tcctgccatc attagagctg ccagtccttc atgtccctag aaatctcaag ctttctcttc  10080
cacatttcaa ggaattgtgt accataagcc atattttat tcctgccatg gcaatatta   10140
cctatgattt ctccctttaaa tcaagtgtca tcacactgaa taccaatgct gaacttttta  10200
accagtcaga tattgttgct catctccttt cttcatcttc atctgtcatt gatgcactgc  10260
```

```
agtacaaatt agagggcacc acaagattga caagaaaaag gggattgaag ttagccacag   10320
ctctgtctct gagcaacaaa tttgtggagg gtagtcataa cagtactgtg agcttaacca   10380
cgaaaaatat ggaagtgtca gtggcaaaaa ccacaaaagc cgaaattcca attttgagaa   10440
tgaatttcaa gcaagaactt aatggaaata ccaagtcaaa acctactgtc tcttcctcca   10500
tggaatttaa gtatgatttc aattcttcaa tgctgtactc taccgctaaa ggagcagttg   10560
accacaagct tagcttggaa agcctcacct cttactttc cattgagtca tctaccaaag    10620
gagatgtcaa gggttcggtt cttctcggg aatattcagg aactattgct agtgaggcca    10680
acacttactt gaattccaag agcacacggt cttcagtgaa gctgcagggc acttccaaaa   10740
ttgatgatat ctggaacctt gaagtaaaag aaaattttgc tggagaagcc acactccaac   10800
gcatatattc cctctgggag cacagtacga aaaccactt acagctagag ggcctctttt    10860
tcaccaacgg agaacataca agcaaagcca ccctggaact ctctccatgg caaatgtcag   10920
ctcttgttca ggtccatgca agtcagccca gttccttcca tgatttccct gaccttggcc   10980
aggaagtggc cctgaatgct aacactaaga accagaagat cagatggaaa aatgaagtcc   11040
ggattcattc tgggtctttc cagagccagg tcgagctttc caatgaccaa gaaaaggcac   11100
accttgacat tgcaggatcc ttagaaggac acctaaggtt cctcaaaaat atcatcctac   11160
cagtctatga caagagctta tgggatttcc taaagctgga tgtaaccacc agcattggta   11220
ggagacagca tcttcgtgtt tcaactgcct ttgtgtacac caaaaacccc aatggctatt   11280
cattctccat ccctgtaaaa gttttggctg ataaattcat tactcctggg ctgaaactaa   11340
atgatctaaa ttcagttctt gtcatgccta cgttccatgt cccattaca gatcttcagg    11400 ttccatcgtg caaacttgac ttcagagaaa tacaaatcta taagaagctg agaacttcat   11460
catttgccct caacctacca acactccccg aggtaaaatt ccctgaagtt gatgtgttaa   11520
caaaatattc tcaaccagaa gactccttga ttcccttttt tgagataacc gtgcctgaat   11580
ctcagttaac tgtgtcccag ttcacgcttc caaaaagtgt ttcagatggc attgctgctt   11640
tggatctaaa tgcagtagcc aacaagatcg cagactttga gttgcccacc atcatcgtgc   11700
ctgagcagac cattgagatt ccctccatta agttctctgt acctgctgga attgtcattc   11760
cttcctttca agcactgact gcacgctttg aggtagactc tcccgtgtat aatgccactt   11820
ggagtgccag tttgaaaaac aaagcagatt atgttgaaac agtcctggat tccacatgca   11880
gctcaaccgt acagttccta gaatatgaac taaatgtttt gggaacacac aaaatcgaag   11940
atggtacgtt agcctctaag actaaaggaa cacttgcaca ccgtgacttc agtgcagaat   12000
atgaagaaga tggcaaattt gaaggacttc aggaatggga aggaaaagcg cacctcaata   12060
tcaaaagccc agcgttcacc gatctccatc tgcgctacca gaaagacaag aaaggcatct   12120
ccacctcagc agcctcccca gccgtaggca ccgtgggcat ggatatggat gaagatgacg   12180
acttttctaa atggaacttc tactacagcc ctcagtcctc tccagataaa aaactcacca   12240
tattcaaaac tgagttgagg gtccgggaat ctgatgagga aactcagatc aaagttaatt   12300
gggaagaaga ggcagcttct ggcttgctaa cctctctgaa agacaacgtg cccaaggcca   12360 cagggtcct tatgattat gtcaacaagt accactggga acacacaggg ctcaccctga    12420
gagaagtgtc ttcaaagctg agaagaaatc tgcagaacaa tgctgagtgg gtttatcaag   12480
gggccattag gcaaattgat gatatcgacg tgaggttcca gaaagcagcc agtggcacca   12540
ctgggaccta ccaagagtgg aaggacaagg cccagaatct gtaccaggaa ctgttgactc   12600
aggaaggcca agccagtttc cagggactca aggataacgt gtttgatggc ttggtacgag   12660
```

```
ttactcaaaa attccatatg aaagtcaagc atctgattga ctcactcatt gattttctga    12720
acttccccag attccagttt ccggggaaac ctgggatata cactagggag gaactttgca    12780
ctatgttcat aagggaggta gggacggtac tgtcccaggt atattcgaaa gtccataatg    12840
gttcagaaat actgttttcc tatttccaag acctagtgat tacacttcct ttcgagttaa    12900
ggaaacataa actaatagat gtaatctcga tgtataggga actgttgaaa gatttatcaa    12960
aagaagccca agaggtattt aaagccattc agtctctcaa gaccacagag gtgctacgta    13020
atcttcagga cctttttacaa ttcattttcc aactaataga agataacatt aaacagctga   13080
aagagatgaa atttacttat cttattaatt atatccaaga tgagatcaac acaatcttca    13140
atgattatat cccatatgtt tttaaattgt tgaaagaaaa cctatgcctt aatcttcata    13200
agttcaatga atttattcaa aacgagcttc aggaagcttc tcaagagtta cagcagatcc    13260
atcaatacat tatggcccctt cgtgaagaat attttgatcc aagtatagtt ggctggacag    13320
tgaaatatta tgaacttgaa gaaaagatag tcagtctgat caagaacctg ttagttgctc     13380
ttaaggactt ccattctgaa tatattgtca gtgcctctaa ctttacttcc caactctcaa    13440
gtcaagttga gcaatttctg cacagaaata ttcaggaata tcttagcatc cttaccgatc    13500
cagatggaaa agggaaagag aagattgcag agctttctgc cactgctcag gaaataatta    13560
aaagccaggc cattgcgacg aagaaaataa tttctgatta ccaccagcag tttagatata    13620
aactgcaaga ttttttcagac caactctctg attactatga aaaatttatt gctgaatcca    13680
aaagattgat tgacctgtcc attcaaaact accacacatt tctgatatac atcacggagt    13740
tactgaaaaa gctgcaatca accacagtca tgaacccta catgaagctt gctccaggag    13800
aacttactat catcctctaa ttttttaaaa gaaatcttca tttattcttc tttttccaatt   13860 gaactttcac atagcacaga aaaaattcaa actgcctata ttgataaaac catacagtga    13920
gccagccttg cagtaggcag tagactataa gcagaagcac atatgaactg gacctgcacc    13980
aaagctggca ccagggctcg gaaggtctct gaactcagaa ggatggcatt ttttgcaagt    14040
taaagaaaat caggatctga gttattttgc taaacttggg ggaggaggaa caaataaatg    14100
gagtctttat tgtgtatcat a                                              14121

<210> SEQ ID NO 2
<211> LENGTH: 20
<212> TYPE: DNA
<213> ORGANISM: Artificial Sequence
<220> FEATURE:
<223> OTHER INFORMATION: ISIS 301012 antisense oligonucleotide

<400> SEQUENCE: 2
gcctcagtct gcttcgcacc                                                   20
```